US011400260B2

(12) United States Patent
Huang et al.

(10) Patent No.: US 11,400,260 B2
(45) Date of Patent: Aug. 2, 2022

(54) CATHETER INSERTION DEVICE

(71) Applicant: C. R. Bard, Inc., Murray Hill, NJ (US)

(72) Inventors: Heqing Huang, Shanghai (CN); Jianjiang Chen, Shanghai (CN); Weng K. Chan, Shanghai (CN)

(73) Assignee: C. R. Bard, Inc., Franklin Lakes, NJ (US)

( * ) Notice: Subject to any disclaimer, the term of this patent is extended or adjusted under 35 U.S.C. 154(b) by 109 days.

(21) Appl. No.: 16/490,023

(22) PCT Filed: Mar. 1, 2017

(86) PCT No.: PCT/CN2017/075370
§ 371 (c)(1),
(2) Date: Aug. 29, 2019

(87) PCT Pub. No.: WO2018/157339
PCT Pub. Date: Sep. 7, 2018

(65) Prior Publication Data
US 2020/0001051 A1    Jan. 2, 2020

(51) Int. Cl.
*A61M 25/06* (2006.01)
*A61M 25/00* (2006.01)
(Continued)

(52) U.S. Cl.
CPC .... *A61M 25/0618* (2013.01); *A61M 25/0631* (2013.01); *A61M 25/0693* (2013.01);
(Continued)

(58) Field of Classification Search
CPC .......... A61M 25/0113; A61M 25/0625; A61M 25/09041; A61M 25/0136;
(Continued)

(56) References Cited

U.S. PATENT DOCUMENTS 2,211,975 A    8/1940    Hendrickson
2,259,488 A    10/1941   Raiche
(Continued)

FOREIGN PATENT DOCUMENTS

AU        691141 B2    5/1998
AU        710967 B2    9/1999
(Continued)

OTHER PUBLICATIONS

U.S. Appl. No. 15/154,384, filed May 13, 2016 Notice of Allowance dated Apr. 29, 2021.
(Continued)

*Primary Examiner* — Nathan R Price
*Assistant Examiner* — Anh Bui
(74) *Attorney, Agent, or Firm* — Rutan & Tucker LLP

(57) ABSTRACT

A tool (10) for inserting a catheter (22) into a body of a patient is provided. The tool (10) comprises: a housing (12, 40, 50) in which at least a portion of the catheter (22) is initially disposed; a needle (16) distally extending from the housing (12, 40, 50), at least a portion of the catheter (22) disposed over the needle (16); a guidewire (32) initially disposed within the needle (16) partially; and an advancement assembly (20) for distally advancing the catheter (22). The housing (12, 40, 50) comprises: a first portion (12A, 42, 52) comprising a distal part (42A, 52A) and a proximal part (42B); and a second portion (12B, 44, 54) engaged with the first portion (12A, 42, 52), wherein the distal part (42A, 52A) of the first portion (12A, 42, 52) is configured to be able to distally slide with respect to the second portion (12B, 44, 54) to release the engagement between the first portion (12A, 42, 52) and the second portion (12B, 44, 54). The advancement assembly (20) includes a safety cap (26) which is initially disposed over the needle (16) and is configured to be locked to the housing (12, 40, 50) when distally sliding
(Continued)

to a position of isolating the tip of the needle (16) within the safety cap (26).

14 Claims, 36 Drawing Sheets

(51) Int. Cl.
    *A61M 25/01* (2006.01)
    *A61M 25/09* (2006.01)
(52) U.S. Cl.
    CPC ..... *A61M 25/0097* (2013.01); *A61M 25/0136* (2013.01); *A61M 25/09041* (2013.01); *A61M 2025/0177* (2013.01); *A61M 2025/09116* (2013.01)
(58) Field of Classification Search
    CPC .......... A61M 25/0097; A61M 25/0693; A61M 25/0631; A61M 25/0618; A61M 2025/09116; A61M 2025/0177
    See application file for complete search history.

(56) References Cited

U.S. PATENT DOCUMENTS

| | | |
|---|---|---|
| 2,330,400 A | 9/1943 | Winder |
| D138,589 S | 8/1944 | Brandenburg |
| 3,185,151 A | 5/1965 | Czomy |
| 3,297,030 A | 1/1967 | Czomy et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,766,916 A | 10/1973 | Moorehead et al. |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,525,157 A | 6/1985 | Vaillancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillar |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,850,961 A | 7/1989 | Wanderer et al. |
| 4,860,757 A | 8/1989 | Lynch et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,668 A | 4/1990 | Haindl et al. |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A | 10/1991 | Chuttani et al. |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,396 A | 3/1992 | Taylor et al. |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada et al. |
| 5,176,650 A | 1/1993 | Haining |

(56) References Cited

U.S. PATENT DOCUMENTS

| | | |
|---|---|---|
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,439,449 A | 8/1995 | Mapes et al. |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,671 A | 3/1996 | Rosen et al. |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Merge et al. |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,697,914 A | 12/1997 | Brimhall |
| 5,700,250 A | 12/1997 | Erskine |
| 5,702,367 A | 12/1997 | Cover et al. |
| 5,702,369 A | 12/1997 | Mercereau |
| 5,704,914 A | 1/1998 | Stocking et al. |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,749,861 A | 5/1998 | Guala et al. |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |

(56) References Cited

U.S. PATENT DOCUMENTS

| | | |
|---|---|---|
| 5,807,350 A | 9/1998 | Diaz |
| 5,810,780 A | 9/1998 | Brimhall et al. |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther et al. |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| D413,382 S | 8/1999 | Maissami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynsk et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,633 A | 10/2000 | Kaji et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,623,456 B1 | 9/2003 | Holdaway et al. |
| 6,626,868 B1 | 9/2003 | Prestidge et al. |
| 6,626,869 B1 | 9/2003 | Bint |
| 6,629,959 B2 | 10/2003 | Kuracina et al. |

(56) References Cited

U.S. PATENT DOCUMENTS

| | | |
|---|---|---|
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tai |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |

(56) References Cited

U.S. PATENT DOCUMENTS

| | | |
|---|---|---|
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,833,201 B2 | 11/2010 | Carlyon et al. |
| 7,850,644 B2 | 12/2010 | Gonzalez et al. |
| 7,857,770 B2 | 12/2010 | Raulerson et al. |
| D634,843 S | 3/2011 | Kim et al. |
| 7,896,862 B2 | 3/2011 | Long |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tai et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| D643,531 S | 8/2011 | van der Weiden |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,323,249 B2 | 12/2012 | White et al. |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,089,674 B2 | 7/2015 | Ginn et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |

(56) References Cited

U.S. PATENT DOCUMENTS

| | | |
|---|---|---|
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| D775,330 S | 12/2016 | Blennow et al. |
| 9,522,254 B2 | 12/2016 | Belson |
| D776,259 S | 1/2017 | Eldredge |
| 9,545,495 B2 | 1/2017 | Goral et al. |
| 9,554,817 B2 | 1/2017 | Goldfarb et al. |
| D779,059 S | 2/2017 | Nino et al. |
| D779,661 S | 2/2017 | McKnight et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| D791,311 S | 7/2017 | Yantz |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| D810,282 S | 2/2018 | Ratjen |
| D815,737 S | 4/2018 | Bergstrom et al. |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,357,635 B2 | 7/2019 | Korkuch et al. |
| 10,384,039 B2 | 8/2019 | Ribelin et al. |
| 10,426,931 B2 | 10/2019 | Blanchard et al. |
| D870,271 S | 12/2019 | Kheradpir et al. |
| D870,883 S | 12/2019 | Harding et al. |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 10,806,906 B2 | 10/2020 | Warring et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long |
| 2005/0273057 A1 | 12/2005 | Popov |
| 2006/0025721 A1 | 2/2006 | Duffy et al. |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |

(56) References Cited

U.S. PATENT DOCUMENTS

| | | |
|---|---|---|
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |
| 2008/0039796 A1 | 2/2008 | Nakajima |
| 2008/0065011 A1 | 3/2008 | Marchand et al. |
| 2008/0082082 A1 | 4/2008 | Carlyon et al. |
| 2008/0097330 A1 | 4/2008 | King et al. |
| 2008/0108911 A1 | 5/2008 | Palmer et al. |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tai et al. |
| 2008/0300574 A1 | 12/2008 | Belson et al. |
| 2009/0018567 A1 | 1/2009 | Escudero et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0016838 A1 | 1/2010 | Butts et al. |
| 2010/0036331 A1 | 2/2010 | Sen |
| 2010/0056910 A1 | 3/2010 | Yanuma |
| 2010/0057183 A1 | 3/2010 | Mangiardi et al. |
| 2010/0087787 A1 | 4/2010 | Woehr et al. |
| 2010/0094116 A1 | 4/2010 | Silverstein |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1 | 8/2010 | Belson |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0158506 A1 | 6/2013 | Harris et al. |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0243734 A1 | 8/2014 | Eubanks et al. |
| 2014/0249488 A1 | 9/2014 | Woehr |
| 2014/0257359 A1 | 9/2014 | Fegels et al. |
| 2014/0276224 A1 | 9/2014 | Ranganathan et al. |
| 2014/0276432 A1 | 9/2014 | Bierman et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0094659 A1* | 4/2015 | Schraga .................. A61M 5/46 604/110 |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0202421 A1 | 7/2015 | Ma et al. |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |

(56) References Cited

U.S. PATENT DOCUMENTS

| | | |
|---|---|---|
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0106959 A1 | 4/2016 | Woehr |
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0206858 A1 | 7/2016 | Ishida |
| 2016/0220161 A1 | 8/2016 | Goral et al. |
| 2016/0220786 A1 | 8/2016 | Mitchell et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1 | 11/2016 | Teoh |
| 2016/0331938 A1* | 11/2016 | Blanchard ......... A61M 25/0618 |
| 2016/0354580 A1 | 12/2016 | Teoh et al. |
| 2016/0361490 A1 | 12/2016 | Phang et al. |
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0043132 A1 | 2/2017 | Ishida |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0209668 A1 | 7/2017 | Belson |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0022358 A1 | 1/2019 | Belson |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0094037 A1 | 3/2020 | Tran et al. |
| 2020/0261696 A1 | 8/2020 | Blanchard |
| 2020/0261703 A1 | 8/2020 | Belson et al. |
| 2020/0316347 A1 | 10/2020 | Belson |
| 2021/0052858 A1 | 2/2021 | Isaacson et al. |
| 2021/0308428 A1 | 10/2021 | Blanchard et al. |
| 2021/0402155 A1 | 12/2021 | Hall et al. |

FOREIGN PATENT DOCUMENTS

| | | |
|---|---|---|
| CN | 1178707 A | 4/1998 |
| CN | 1319023 A | 10/2001 |
| CN | 1523970 A | 8/2004 |
| CN | 1871043 A | 11/2006 |
| CN | 101242868 A | 8/2008 |
| CN | 101293122 A | 10/2008 |
| CN | 101417159 A | 4/2009 |
| CN | 101784300 A | 7/2010 |
| CN | 102099075 A | 6/2011 |
| CN | 102939129 A | 2/2013 |
| CN | 104689456 A | 6/2015 |
| CN | 105073174 A | 11/2015 |
| CN | 105188826 A | 12/2015 |
| CN | 105705191 A | 6/2016 |
| DE | 20210394 U1 | 9/2002 |
| EP | 0314470 A2 | 5/1989 |
| EP | 417764 A1 | 3/1991 |
| EP | 475857 A1 | 3/1992 |
| EP | 515710 A1 | 12/1992 |
| EP | 567321 A2 | 10/1993 |
| EP | 552020 A2 | 5/1995 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |
| EP | 942761 A1 | 9/1999 |
| EP | 1075850 A2 | 2/2001 |
| EP | 1378263 A2 | 1/2004 |
| EP | 1418971 A2 | 5/2004 |
| EP | 1457229 A1 | 9/2004 |
| EP | 1611916 A1 | 1/2006 |
| EP | 1907042 A2 | 4/2008 |
| EP | 2150304 A2 | 2/2010 |
| EP | 2272432 A1 | 1/2011 |
| EP | 2569046 A1 | 3/2013 |
| GB | 2529270 A * | 2/2016 ........ A61M 25/0625 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 A | 7/2013 |
| JP | 2018-118079 A | 8/2018 |
| WO | 83/01575 A1 | 5/1983 |
| WO | 1983001575 A1 | 5/1983 |
| WO | 1992013584 A1 | 8/1992 |
| WO | 92/22344 A1 | 12/1992 |
| WO | 1992022344 A1 | 12/1992 |
| WO | 1995011710 A1 | 5/1995 |
| WO | 95/19193 A1 | 7/1995 |
| WO | 1995019193 A1 | 7/1995 |
| WO | 95/23003 A1 | 8/1995 |
| WO | 1995023003 A1 | 8/1995 |
| WO | 96/32981 A1 | 10/1996 |
| WO | 1996032981 A1 | 10/1996 |
| WO | 1996040359 A1 | 12/1996 |
| WO | 97/05912 A2 | 2/1997 |
| WO | 1997005912 A2 | 2/1997 |
| WO | 97/21458 A1 | 6/1997 |
| WO | 1997021458 A1 | 6/1997 |
| WO | 1997045151 A1 | 12/1997 |
| WO | 98/24494 A1 | 6/1998 |
| WO | 1998024494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06226 A1 | 2/2000 |
| WO | 00/12160 A1 | 3/2000 |
| WO | 2000012167 A1 | 3/2000 |
| WO | 00/47256 A1 | 8/2000 |
| WO | 00/67829 A1 | 11/2000 |
| WO | 2001007103 A1 | 2/2001 |
| WO | 01/26725 A1 | 4/2001 |
| WO | 2002041932 A2 | 5/2002 |
| WO | 02/066093 A2 | 8/2002 |
| WO | 03/11381 A1 | 2/2003 |
| WO | 03/043686 A1 | 5/2003 |
| WO | 03/43686 A1 | 5/2003 |
| WO | 03/47675 A2 | 6/2003 |
| WO | 03/047675 A2 | 6/2003 |
| WO | 2004/018031 A2 | 3/2004 |
| WO | 2005002659 A1 | 1/2005 |

(56) References Cited

FOREIGN PATENT DOCUMENTS

| | | |
|---|---|---|
| WO | 2004106203 A3 | 3/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |
| WO | 2008/131300 A2 | 10/2008 |
| WO | 2008137956 A2 | 11/2008 |
| WO | 2009/001309 A1 | 12/2008 |
| WO | 2008147600 A1 | 12/2008 |
| WO | 2009031161 A1 | 3/2009 |
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011143621 A1 | 11/2011 |
| WO | 2012106266 A1 | 8/2012 |
| WO | 2012154277 A1 | 11/2012 |
| WO | 2012174109 A1 | 12/2012 |
| WO | 2013119557 A1 | 8/2013 |
| WO | 2013126446 A1 | 8/2013 |
| WO | 2013187827 A1 | 12/2013 |
| WO | 2014006403 A1 | 1/2014 |
| WO | 2014029424 A1 | 2/2014 |
| WO | 2014074417 A2 | 5/2014 |
| WO | 2014081942 A1 | 5/2014 |
| WO | 2014/123848 A1 | 8/2014 |
| WO | 2014120741 A1 | 8/2014 |
| WO | 2014133617 A1 | 9/2014 |
| WO | 2014140257 A1 | 9/2014 |
| WO | 2014140265 A1 | 9/2014 |
| WO | 2014/165783 A1 | 10/2014 |
| WO | 2014158908 A1 | 10/2014 |
| WO | 2014182421 A1 | 11/2014 |
| WO | 2014197656 A1 | 12/2014 |
| WO | 2014204593 A1 | 12/2014 |
| WO | 2015017136 A1 | 2/2015 |
| WO | 2015024904 A1 | 2/2015 |
| WO | 2015035393 A1 | 3/2015 |
| WO | 2015058136 A1 | 4/2015 |
| WO | 15108913 A1 | 7/2015 |
| WO | 2015/168655 A2 | 11/2015 |
| WO | 15164912 A1 | 11/2015 |
| WO | 2016/037127 A1 | 3/2016 |
| WO | 16178974 A1 | 11/2016 |
| WO | 2018/049413 A1 | 3/2018 |
| WO | 2018170349 A1 | 9/2018 |
| WO | 2019173641 A1 | 9/2019 |

OTHER PUBLICATIONS

U.S. Appl. No. 15/154,384, filed May 13, 2016 Notice of Allowance dated Mar. 17, 2021.
U.S. Appl. No. 15/862,380, filed Jan. 4, 2018 Notice of Allowance dated Jun. 16, 2021.
U.S. Appl. No. 16/292,076, filed Mar. 4, 2019 Corrected Notice of Allowance dated Feb. 25, 2021.
U.S. Appl. No. 16/295,906, filed Mar. 7, 2019 Notice of Allowance dated Mar. 4, 2021.
U.S. Appl. No. 16/296,087, filed Mar. 7, 2019 Non-Final Office Action dated Mar. 26, 2021.
U.S. Appl. No. 16/296,087, filed Mar. 7, 2019 Restriction Requirement dated Feb. 8, 2021.
U.S. Appl. No. 16/389,719, filed Apr. 19, 2019 Final Office Action dated Jun. 14, 2021.
U.S. Appl. No. 16/389,719, filed Apr. 19, 2019 Non-Final Office Action dated Mar. 19, 2021.
U.S. Appl. No. 16/529,622, filed Aug. 1, 2019 Non-Final Office Action dated May 7, 2021.
U.S. Appl. No. 29/658,136, filed Jul. 27, 2018 Notice of Allowance dated Mar. 23, 2021.
EP 16797029.2 filed Nov. 21, 2017 Office Action dated Mar. 27, 2020.
EP17849786.3 filed Apr. 12, 2019 Extended European Search Report dated May 13, 2020.
U.S. Appl. No. 14/250,093, filed Apr. 10, 2014 Patent Board Decision dated Jun. 8, 2020.
U.S. Appl. No. 15/154,384, filed May 13, 2016 Final Office Action dated Nov. 27, 2019.
U.S. Appl. No. 15/727,528, filed Oct. 6, 2017 Final Office Action dated Jan. 28, 2020.
U.S. Appl. No. 15/727,528, filed Oct. 6, 2017 Notice of Allowance dated Mar. 27, 2020.
U.S. Appl. No. 15/862,380, filed Jan. 4, 2018 Restriction Requirement dated Dec. 23, 2019.
U.S. Appl. No. 15/869,872, filed Jan. 12, 2018 Non-Final Office Action dated Apr. 10, 2020.
U.S. Appl. No. 15/951,931, filed Apr. 12, 2018 Non-Final Office Action dated Nov. 19, 2019.
U.S. Appl. No. 15/951,931, filed Apr. 12, 2018 Notice of Allowance dated Feb. 20, 2020.
U.S. Appl. No. 15/951,931, filed Apr. 12, 2018 Notice of Allowability dated Apr. 16, 2020.
U.S. Appl. No. 15/951,954, filed Apr. 12, 2018 Notice of Allowance dated Feb. 23, 2020.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 29/654,521, filed Jun. 25, 2018 Restriction Requirement dated Apr. 8, 2020.
U.S. Appl. No. 29/654,527, filed Jun. 25, 2018 Restriction Requirement dated Mar. 10, 2020.
U.S. Appl. No. 29/658,136, filed Jul. 27, 2018 Restriction Requirement dated May 11, 2020.
U.S. Appl. No. 14/250,093, filed Apr. 10, 2014 Notice of Allowance dated Aug. 19, 2020.
U.S. Appl. No. 14/866,738, filed Sep. 25, 2015 Patent Board Decision dated Jul. 13, 2020.
U.S. Appl. No. 15/154,384, filed May 13, 2016 Non-Final Office Action dated Jun. 26, 2020.
U.S. Appl. No. 15/862,380, filed Jan. 4, 2018 Non-Final Office Action dated Jul. 9, 2020.
U.S. Appl. No. 15/869,872, filed Jan. 12, 2018 Final Office Action dated Jun. 25, 2020.
U.S. Appl. No. 16/292,076, filed Mar. 4, 2019 Non-Final Office Action dated Aug. 10, 2020.
U.S. Appl. No. 16/295,906, filed Mar. 7, 2019 Non-Final Office Action dated Sep. 4, 2020.
U.S. Appl. No. 29/654,521, filed Jun. 25, 2018 Notice of Allowance dated Aug. 17, 2020.
U.S. Appl. No. 29/654,527, filed Jun. 25, 2018 Notice of Allowance dated Aug. 18, 2020.
U.S. Appl. No. 29/658,136, filed Jul. 27, 2018 Non-Final Office Action dated Sep. 9, 2020.
U.S. Appl. No. 15/154,808, filed May 13, 2016 Advisory Action dated Oct. 26, 2018.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Notice of Allowance dated Apr. 16, 2019.
U.S. Appl. No. 15/154,808, filed May 13, 2016 Restriction Requirement dated Jan. 3, 2018.
U.S. Appl. No. 15/377,880, filed Dec. 13, 2016 Final Office Action dated Oct. 19, 2018.
U.S. Appl. No. 15/377,880, filed Dec. 13, 2016 Non-Final Office Action dated May 14, 2018.

(56) References Cited

OTHER PUBLICATIONS

U.S. Appl. No. 15/481,773, filed Apr. 7, 2017 Final Office Action dated Jan. 10, 2019.
U.S. Appl. No. 15/481,773, filed Apr. 7, 2017 Non-Final Office Action dated Jun. 29, 2018.
U.S. Appl. No. 15/608,802, filed May 30, 2017 Non-Final Office Action dated Jun. 6, 2019.
U.S. Appl. No. 15/692,915, filed Aug. 31, 2017 Non-Final Office Action dated Jan. 29, 2018.
U.S. Appl. No. 15/702,537, filed Sep. 12, 2017 Final Office Action dated Mar. 8, 2019.
U.S. Appl. No. 15/702,537, filed Sep. 12, 2017 Non-Final Office Action dated Nov. 29, 2018.
U.S. Appl. No. 15/702,537, filed Sep. 12, 2017 Notice of Allowance dated Jul. 31, 2019.
U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
U.S. Appl. No. 15/951,954, filed Apr. 12, 2018 Non-Final Office Action dated Nov. 4, 2019.
U.S. Appl. No. 29/536,043, filed Aug. 12, 2015 Final Office Action dated Mar. 26, 2018.
U.S. Appl. No. 29/536,043, filed Aug. 12, 2015 Non-Final Office Action dated Aug. 31, 2017.
U.S. Appl. No. 29/545,436, filed Nov. 12, 2015 Final Office Action dated Mar. 26, 2018.
U.S. Appl. No. 29/545,436, filed Nov. 12, 2015 Non-Final Office Action dated Sep. 12, 2017.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
JP 2016-563441 filed Oct. 19, 2016 Office Action dated Jan. 25, 2019.
JP 2018-039302 filed Mar. 6, 2018 Office Action dated Feb. 20, 2019.
Menlo Care, Landmark™ Aquavene® Catheters Brochure, 1992.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/CN2017/075370 filed Mar. 1, 2017 International Search Report and Written Opinion dated Nov. 30, 2017.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PCT/US2017/051214 filed Sep. 12, 2017 International Search Report and Written Opinion dated Nov. 13, 2017.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene@, JVAN vol. 1, No. 3, Spring 1991.
RU 2017141812 filed Nov. 30, 2017 Office Action dated Jan. 31, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
U.S. Appl. No. 14/099,050, filed Dec. 6, 2013 Advisory Action dated Jun. 1, 2017.
U.S. Appl. No. 14/099,050, filed Dec. 6, 2013 Final Office Action dated Jan. 30, 2017.
PCT/US2019/021231 filed Mar. 7, 2019 International Search Report and Written Opinion, dated Jun. 27, 2019.
U.S. Appl. No. 14/866,738, filed Sep. 25, 2015 Notice of Allowance dated Sep. 24, 2020.
U.S. Appl. No. 15/154,384, filed May 13, 2016 Final Office Action dated Dec. 24, 2020.
U.S. Appl. No. 15/862,380, filed Jan. 4, 2018 Final Office Action dated Oct. 26, 2020.
U.S. Appl. No. 15/869,872, filed Jan. 12, 2018 Advisory Action dated Sep. 23, 2020.
U.S. Appl. No. 16/292,076, filed Mar. 4, 2019 Notice of Allowance dated Feb. 4, 2021.
U.S. Appl. No. 16/295,906, filed Mar. 7, 2019 Final Office Action dated Dec. 22, 2020.
U.S. Appl. No. 16/529,602, filed Aug. 1, 2019 Notice of Allowance dated Jan. 19, 2021.
U.S. Appl. No. 29/654,521, filed Jun. 25, 2018 Notice of Allowability dated Sep. 30, 2020.

(56) References Cited

OTHER PUBLICATIONS

U.S. Appl. No. 29/654,527, filed Jun. 25, 2018 Notice of Allowability dated Sep. 30, 2020.
Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intima™ Integrated Safety IV Catheter Brochure, © 2001.
Becton Dickinson, Insyte® AutoGuard™ Shielded I.V. Catheter Brochure, 1998.
CA 2,799,360 filed May 13, 2011 Office Action dated Jun. 7, 2017.
CN 201180029526.7 filed Dec. 14, 2012 First Office Action dated Apr. 21, 2014.
CN 201280008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201380073657.4 filed Aug. 21, 2015 Office Action dated Jun. 28, 2017.
CN 201380073657.4 filed Aug. 21, 2015 Office Action dated Mar. 2, 2018.
CN 201480019467.9 filed Sep. 29, 2015 Office Action dated Apr. 6, 2017.
CN 201510079782.7 filed Feb. 13, 2015 Office Action dated Dec. 30, 2016.
CN 201510079782.7 filed Feb. 13, 2015 Office Action dated Feb. 5, 2018.
CN 201510079782.7 filed Feb. 13, 2015 Office Action dated Sep. 19, 2017.
CN 201580022407.7 filed Nov. 2, 2016 Office Action dated Jan. 31, 2019.
CN 201580022407.7 filed Nov. 2, 2016 Office Action dated Sep. 16, 2019.
Cook Medical "Lunderquist Extra-Stiff wire guide" (2012).
Endovascular Today "Coiled Stainless Steel Guidewires" Buyer's Guide pp. 13-20, (2012).
EP 07783404.2 filed Jan. 19, 2009 Office Action dated Apr. 16, 2019.
EP 07783404.2 filed Jan. 19, 2009 Office Action dated Mar. 7, 2018.
EP 10075422.5 filed Jul. 5, 2008 European search report and written opinion dated Dec. 1, 2010.
EP 11781384.0 filed Sep. 21, 2012 Extended European Search Report dated Oct. 31, 2017.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 12782187.4 filed Sep. 10, 2013 Office Action dated Apr. 24, 2018.
EP 12782187.4 filed Sep. 10, 2013 Office Action dated Nov. 28, 2018.
EP 13876666.2 filed Sep. 7, 2015 Extended European Search Report dated Sep. 20, 2016.
EP 15785819.2 filed Dec. 2, 2016 Extended European Search Report dated Dec. 4, 2017.
EP 16797029.2 filed Nov. 21, 2017 Extended European Search Report dated May 3, 2018.
EP 16797047.4 filed Dec. 6, 2017 Supplemental European Search Report dated Jan. 9, 2019.
EP 19181963.0 filed Jun. 24, 2019 Extended European Search Report dated Jul. 16, 2019.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.
International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 First Office Action dated Feb. 19, 2015.
JP 2013-510353 filed Oct. 31, 2012 Office Action dated Dec. 15, 2016.
JP 2013-510353 filed Oct. 31, 2012 Second Office Action dated Jan. 28, 2016.
JP 2015-560173 filed Aug. 28, 2015 Office Action dated Aug. 2, 2018.
JP 2015-560173 filed Aug. 28, 2015 Office Action dated Sep. 19, 2017.
JP 2016-107046 filed May 30, 2016 Office Action dated Apr. 26, 2017.
JP 2016-107046 filed May 30, 2016 Office Action dated Jul. 28, 2016.
JP 2016-107046 filed May 30, 2016 Office Action dated Nov. 7, 2017.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Final Office Action dated Dec. 2, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
U.S. Appl. No. 14/192,541, filed Feb. 27, 2014 Notice of Allowance dated Dec. 6, 2016.
U.S. Appl. No. 14/192,541, filed Feb. 27, 2014 Notice of Corrected Allowability dated Mar. 8, 2017.
U.S. Appl. No. 14/250,093, filed Apr. 10, 2014 Advisory Action dated May 19, 2017.
U.S. Appl. No. 14/250,093, filed Apr. 10, 2014 Examiner's Answer dated Jun. 20, 2018.
U.S. Appl. No. 14/250,093, filed Apr. 10, 2014 Final Office Action dated Mar. 9, 2017.
U.S. Appl. No. 14/250,093, filed Apr. 10, 2014 Final Office Action dated Nov. 6, 2017.
U.S. Appl. No. 14/250,093, filed Apr. 10, 2014 Non-Final Office Action dated Nov. 16, 2016.
U.S. Appl. No. 14/250,093, filed Apr. 10, 2014 Panel Decision dated Jul. 14, 2017.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Final Office Action dated May 11, 2018.

(56) References Cited

OTHER PUBLICATIONS

U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Nov. 29, 2016.
U.S. Appl. No. 14/585,800, filed Dec. 30, 2014 Non-Final Office Action dated Nov. 3, 2017.
U.S. Appl. No. 14/585,800, filed Dec. 30, 2014 Non-Final Office Action dated Oct. 8, 2015.
U.S. Appl. No. 14/585,800, filed Dec. 30, 2014 Notice of Allowance dated Feb. 25, 2019.
U.S. Appl. No. 14/585,800, filed Dec. 30, 2014 Notice of Allowance dated Jul. 3, 2017.
U.S. Appl. No. 14/702,580, filed May 1, 2015 Advisory Action dated Nov. 13, 2017.
U.S. Appl. No. 14/702,580, filed May 1, 2015 Final Office Action dated Sep. 1, 2017.
U.S. Appl. No. 14/702,580, filed May 1, 2015 Non-Final Office Action dated May 3, 2017.
U.S. Appl. No. 14/702,580, filed May 1, 2015 Notice of Allowance dated Dec. 8, 2017.
U.S. Appl. No. 14/750,658, filed Jun. 25, 2016 Non-Final Office Action dated Mar. 9, 2017.
U.S. Appl. No. 14/750,658, filed Jun. 25, 2016 Notice of Allowance dated Jul. 20, 2017.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/846,387, filed Sep. 4, 2015 Non-Final Office Action dated Sep. 22, 2017.
U.S. Appl. No. 14/846,387, filed Sep. 4, 2015 Notice of Allowance dated Oct. 29, 2018.
U.S. Appl. No. 14/866,441, filed Sep. 25, 2015 Advisory Action dated Dec. 22, 2016.
U.S. Appl. No. 14/866,441, filed Sep. 25, 2015 Final Office Action dated Jun. 5, 2018.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Apr. 7, 2017.
U.S. Appl. No. 14/866,441, filed Sep. 25, 2015 Non-Final Office Action dated Mar. 14, 2016.
U.S. Appl. No. 14/866,441, filed Sep. 25, 2015 Notice of Allowance dated Oct. 17, 2018.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Nov. 6, 2017.
U.S. Appl. No. 14/866,738, filed Sep. 25, 2015 Non-Final Office Action dated Oct. 31, 2016.
U.S. Appl. No. 14/866,738, filed Sep. 25, 2015 Notice of Panel Decision dated Jun. 23, 2017.
U.S. Appl. No. 14/876,735, filed Oct. 6, 2015 Non-Final Office Action dated Mar. 30, 2017.
U.S. Appl. No. 15/154,384, filed May 13, 2016 Non-Final Office Action dated Jun. 28, 2019.
U.S. Appl. No. 15/154,384, filed May 13, 2016 Restriction Requirment dated Jan. 25, 2019.
U.S. Appl. No. 16/296,087, filed Mar. 7, 2019 Final Office Action dated Sep. 10, 2021.
U.S. Appl. No. 16/450,800, filed Jun. 24, 2019 Non-Final Office Action dated Jul. 9, 2021.
U.S. Appl. No. 16/450,800, filed Jun. 24, 2019 Notice of Allowance dated Nov. 3, 2021.
U.S. Appl. No. 16/529,622, filed Aug. 1, 2019 Notice of Allowance dated Aug. 23, 2021.

* cited by examiner

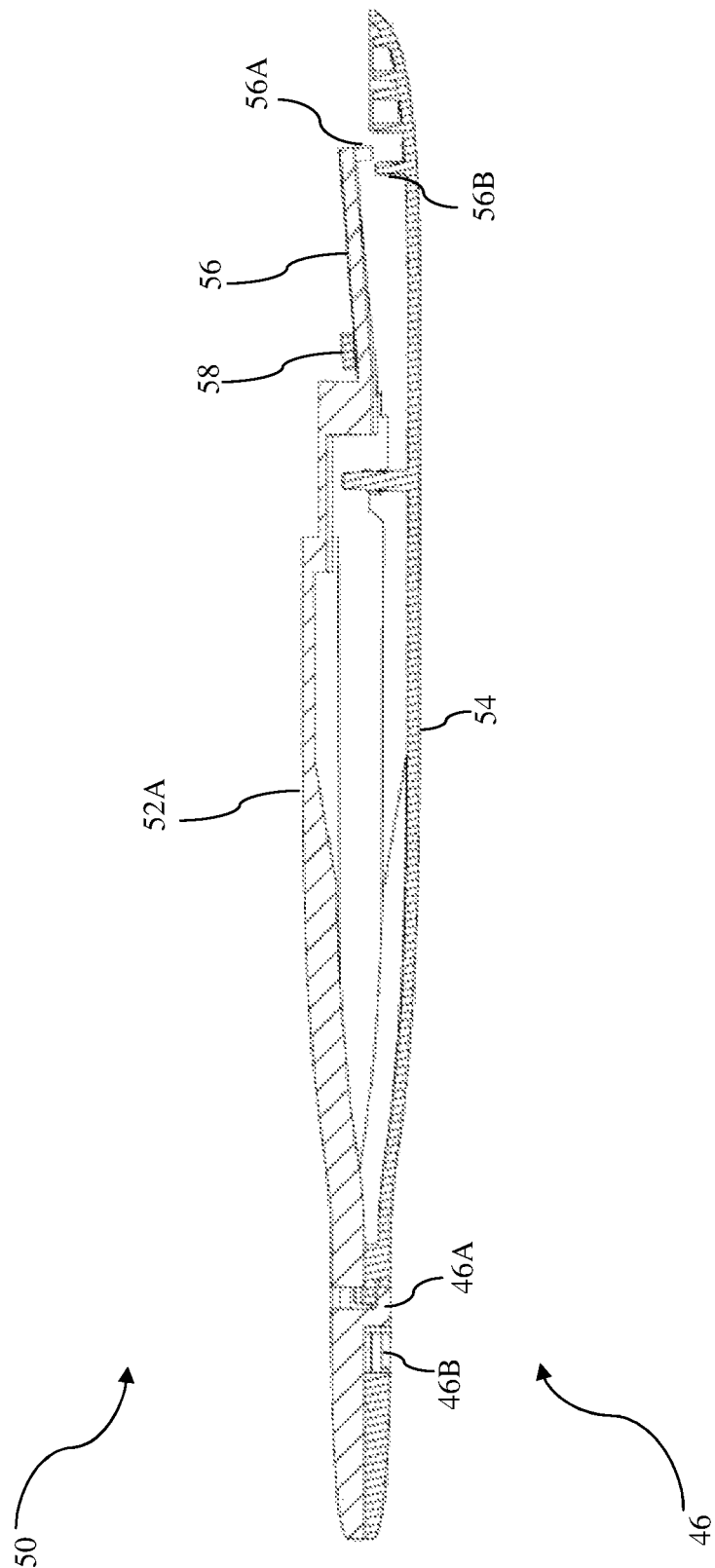

Partially enlarged view C

Partially enlarged view D

CATHETER INSERTION DEVICE

This application is a U.S. national stage application from International Patent Application No. PCT/CN2017/075370, filed Mar. 1, 2017, which is incorporated by reference in its entirety into this application.

TECHNICAL FIELD

The present invention relates to medical devices, more particularly, a catheter insertion device for inserting a catheter into a body of a patient.

BRIEF SUMMARY

Embodiments of the present invention are directed to an insertion tool for inserting a catheter or other tubular medical device into a body of a patient. The insertion tool in one embodiment integrates needle insertion, guidewire advancement, a needle distally extending from the housing and catheter insertion in a single device to provide for a catheter deployment procedure.

In one embodiment, the catheter insertion tool of the present invention comprises a housing, a safety cap slidable along the needle, wherein the safety cap is configured to be locked to the housing when distally sliding to a position of isolating the tip of the needle within the safety cap.

In an embodiment, the safety cap includes a first portion wrapping the needle and a second portion slidably attached to a rail, the rail being an integral part of or fixated to the housing. In an alternative embodiment, the catheter insertion tool further comprises a catheter hub which is connected to the safety cap until the safety cap is locked to the housing when distally sliding to the position of isolating the tip of the needle.

In one embodiment, the housing of the catheter insertion tool of the present invention comprises a first portion comprising a distal part and a proximal part, and a second portion engaged with the first portion, wherein the distal part of the first portion is configured to be able to distally slide with respect to the second portion to release the engagement between the first portion and the second portion.

In an alternative embodiment, the proximal part of the first portion of the housing is fixated to the second portion. In an alternative embodiment, a hook is disposed on an inner surface of the distal part of the first portion, the hook having a tip extending toward the proximal end of the housing, and a slot is disposed on the second housing portion, wherein the slot receives the hook when the first portion and the second portion are engaged, and the hook is released from the slot when the distal part of the first portion is slid distally such that the first portion is released from the second portion.

In an alternative embodiment, wherein the proximal end of the distal part of the first portion of the housing is configured to be axially locked to the second portion of the housing, and the distal part of the first portion is configured to be able to distally slide with respect to the second portion when the locking between the proximal end of the distal part of the first portion and the second portion is released, so as to release the engagement between the first portion and the second portion. In an alternative embodiment, the proximal end of the distal part of the first portion is flexible and is biased toward the second portion when the proximal end of the distal part of the first portion is axially locked to the second portion. In an alternative embodiment, the proximal end of the distal part of the first portion is biased toward the second portion by a slider, and wherein when the slider is distally moved to a certain position, the proximal end of the distal part of the first portion is unbiased and the locking between the proximal end of the distal part of the first portion and the second portion is released.

In an alternative embodiment, a first protrusion extends from the proximal end of the distal part toward the second portion of the housing, and a second protrusion extends from the second portion toward the proximal end of the distal part of the first portion of the housing, and when the proximal end of the distal part of the first portion is biased toward the second portion and the first protrusion is proximal relative to the second protrusion, the proximal end of the distal part of the first portion is axially locked to the second portion.

In one embodiment, a septum for a catheter insertion tool of the present invention comprises a cylindrical main body and a first protrusion which extends from a central portion of a top surface of the main body.

In an alternative embodiment, the septum of the present invention further includes a slit formed within the septum along the longitudinal axis of the septum. Alternatively, the slit is formed within the first protrusion. Alternatively, the slit extends through the septum. Alternatively, the slit is enlarged when a needle extends through the slit and is closed when the needle is withdrawn from the septum. Alternatively, the outer diameter of the main body of the septum is larger than the inner diameter of a lumen of the catheter insertion tool before the septum is installed in the lumen. In an alternative embodiment, the septum of the present invention further includes a second protrusion which extends from a central portion of a bottom surface of the main body opposite to the top surface.

In one embodiment, a septum for a catheter insertion tool of the present invention comprises a circular end portion and a tubular portion extending from the peripheral of the circular end portion. In an alternative embodiment, the septum of the present invention further includes a protrusion extending from a central portion of a surface of the circular end portion opposite to the tubular portion. Alternatively, a slit is formed within the end portion. Alternatively, the slit is formed within the protrusion. Alternatively, the slit extends through the end portion. Alternatively, the slit is enlarged when a needle extends through the slit and is closed when the needle is withdrawn.

In one embodiment, a guidewire advancement device for a catheter insertion tool of the present invention, comprising: a pushing block, including a hole extending through the pushing block from a top surface to a bottom surface of the pushing block, wherein a first sidewall of the hole is in the form of a planar curve; and a rail including a groove aligned with the hole in the longitudinal direction of the catheter insertion tool. In an alternative embodiment, the hole has a second sidewall opposite to the first sidewall is straight, the minimum distance between the first and second sidewalls is wide enough to allow free longitudinal movement of a guidewire and is narrow enough to restrict sway of the guidewire.

In an alternative embodiment, the guidewire advancement device further comprises an anchor point to which one end of a guidewire is fixated, and the guidewire proximally extends from the anchor point, enters the hole via a first potion of the rail, extends away from the hole and distally extends into a second portion of the rail.

In one embodiment, a guidewire advancement device for a catheter insertion tool of the present invention comprises a wheel and a rack configured to rotate the wheel such that a guidewire is driven around the wheel. Alternatively, the guidewire advancement device further comprises a gear coaxially fixed to the wheel, wherein the rack includes teeth to engage the gear. Alternatively, the guidewire advancement device further comprises at least one idler for restricting the guidewire against the peripheral surface of the wheel. Alternatively, the guidewire advancement device further comprises a pipe rail for guiding movement of the guidewire.

In one embodiment, the insertion tool of the present invention comprises a housing in which at least a portion of the catheter is initially disposed, a needle distally extending from the housing, at least a portion of the catheter disposed over the needle, and an advancement assembly for distally advancing the catheter, wherein the housing comprises a first portion comprising a distal part and a proximal part and a second portion engaged with the first portion, wherein the distal part of the first portion is configured to be able to distally slide with respect to the second portion to release the engagement between the first portion and the second portion, and wherein the advancement assembly includes a safety cap which is initially disposed over the needle and is configured to be locked to the housing when distally sliding to a position of isolating the tip of the needle within the safety cap. In an alternative embodiment, the engagement of the first and second portions of the housing is released in preparation for sliding the safety cap to the position isolating the tip of the needle within the safety cap.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more detailed description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 5A-5C are side views of a housing of the catheter insertion tool according to one embodiment of the present invention;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including", "has" and "having" as used herein, including the claims, shall have the same meaning as the word "comprising". Unless specifically indicated otherwise, the word "initially" refers to the state of the insertion tool of the present invention when it is still in the assembled status as delivered to a health-care institution such as a hospital or clinic (or to a patient for use by the patient himself or herself or by the patient's personal care assistant) and has not been operated or used. Unless specifically indicated otherwise, "axial" or "axially" refers to the longitudinal direction of the insertion tool, which is also the orientation of the needle.

Embodiments of the present invention are generally directed to a tool for assisting with the placement into a patient of a catheter or other tubular medical device. For example, catheters of various lengths are typically placed into a body of a patient so as to establish access to the patient's vasculature and enable the infusion of medicaments or aspiration of body fluids. The catheter insertion tool to be described herein facilitates such catheter placement. Note that, while the discussion below focuses on the placement of catheter of a particular type and relatively shout length, catheters of a variety of types, sizes, and lengths can be inserted via the present device, including peripheral IV's intermediate or extended dwell catheters, PICC's, central venous catheters, etc. In one embodiment, catheters having any length are possible.

Figure 1:
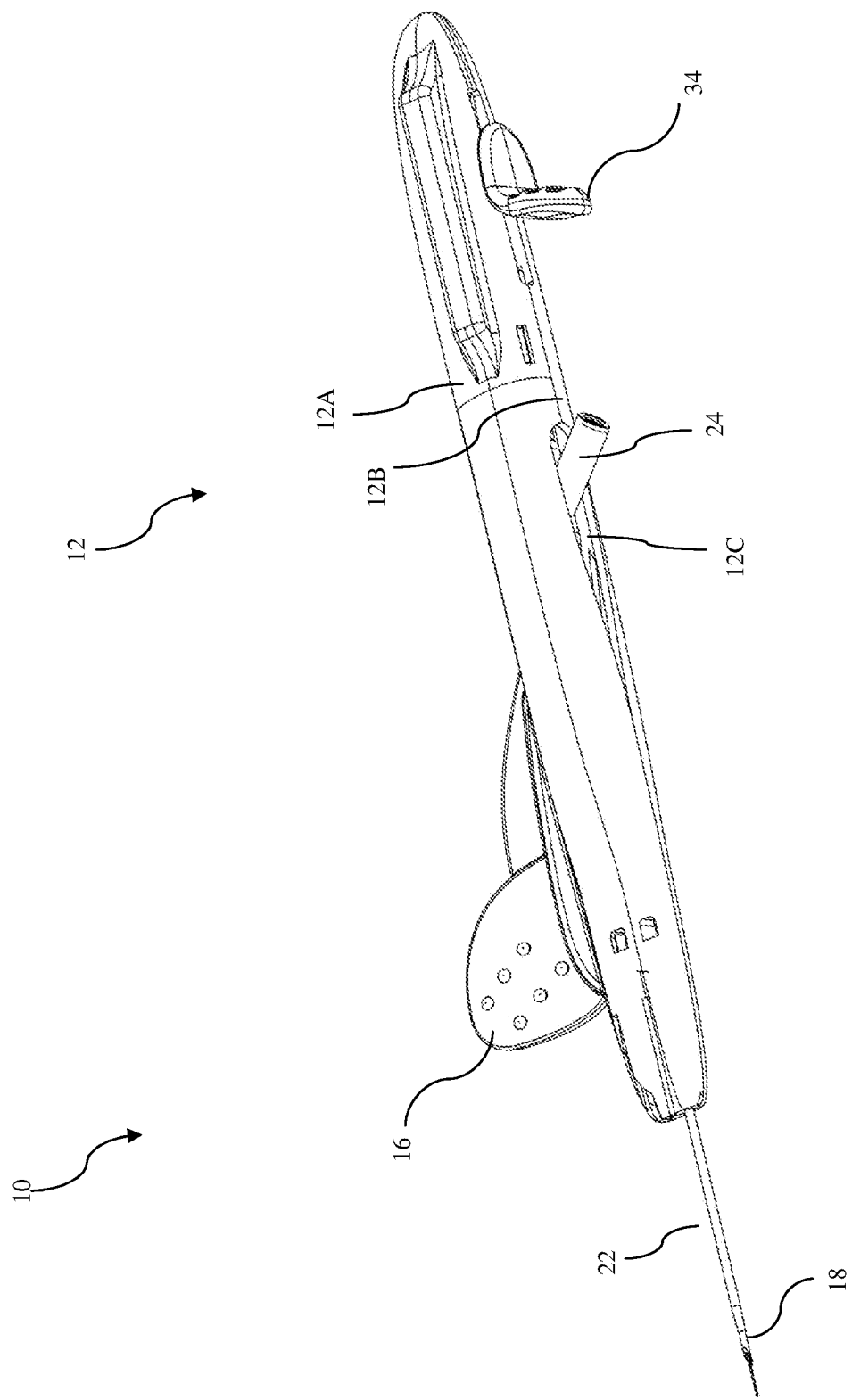
FIG. 1 is a perspective view of a insertion tool according to one embodiment of the present invention.
Figure 2:
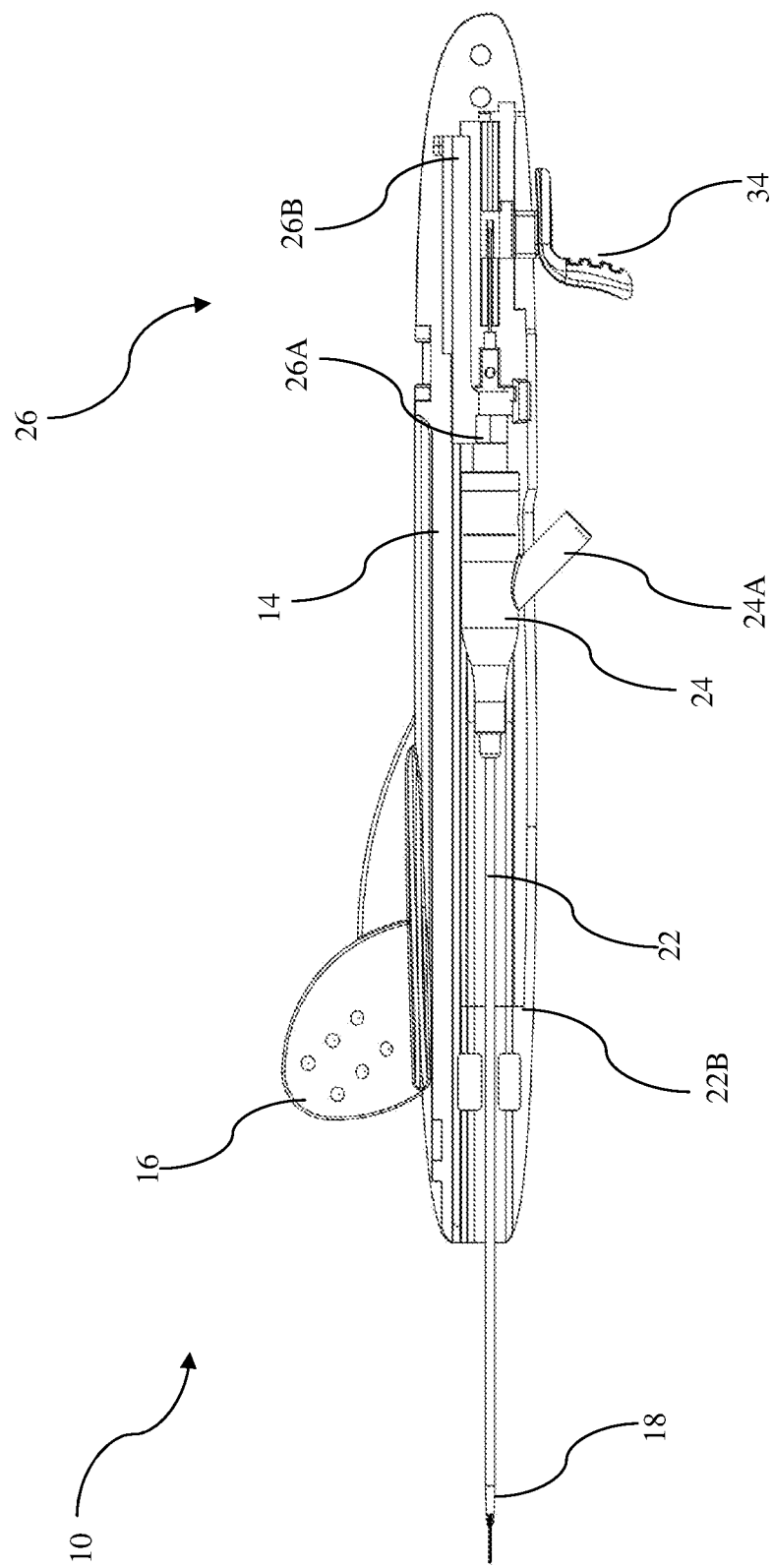
FIG. 2 is a top view of the cross section of the insertion tool of FIG. 1.

Reference is first made to FIG. 1 and FIG. 2, which depict various details of a catheter insertion tool (also referred to "insertion tool" hereinafter), generally depicted at 10, according to one embodiment. As shown in FIG. 1, which is the perspective view of the insertion tool, the insertion tool 10 includes a housing 12 which in turn includes a first portion 12A and a second portion 12B.

In one embodiment, the first portion 12A of the housing 12 is separably engaged with a second portion 12B of the housing 12. In one embodiment, the first portion 12A is able to be distally slide with respect to the second portion 12B to release the engagement. Details on the engagement and release will be provided later.

FIG. 2 is a top view of the cross section of the insertion tool. In one embodiment, as shown in FIG. 2, the insertion tool 10 includes a rail 14 which is integral part of the housing 12 or is an independent element but fixated to the housing 12. For example, the rail 14 can be an integral portion of the first portion 12A (as shown in FIG. 1) of the housing 12 or the second portion 12B of the housing 12, or be fixated to the housing 12 by molding or assembling.

The insertion tool 10 further includes a handle 16 for a clinician to stably hold the tool 10 while operating the tool. In one embodiment, the handle 16 extends from the rail 14. In other embodiments, the handle 16 extends from the housing 12, wherein the handle is disposed on the first portion 12A or the second portion 12B of the housing 12. In one embodiment, one surface of the handle 16 includes small protrusions in order to increase the friction. In another embodiment, the surface of the handle 16 includes other structures that can increase the friction, for example, grooves, wales, frosted surface and so on. Such protrusions or similar structures on the surfaces of the handle 16 improve the operational stability when the user such as a clinician operates the insertion tool.

Figure 3A:
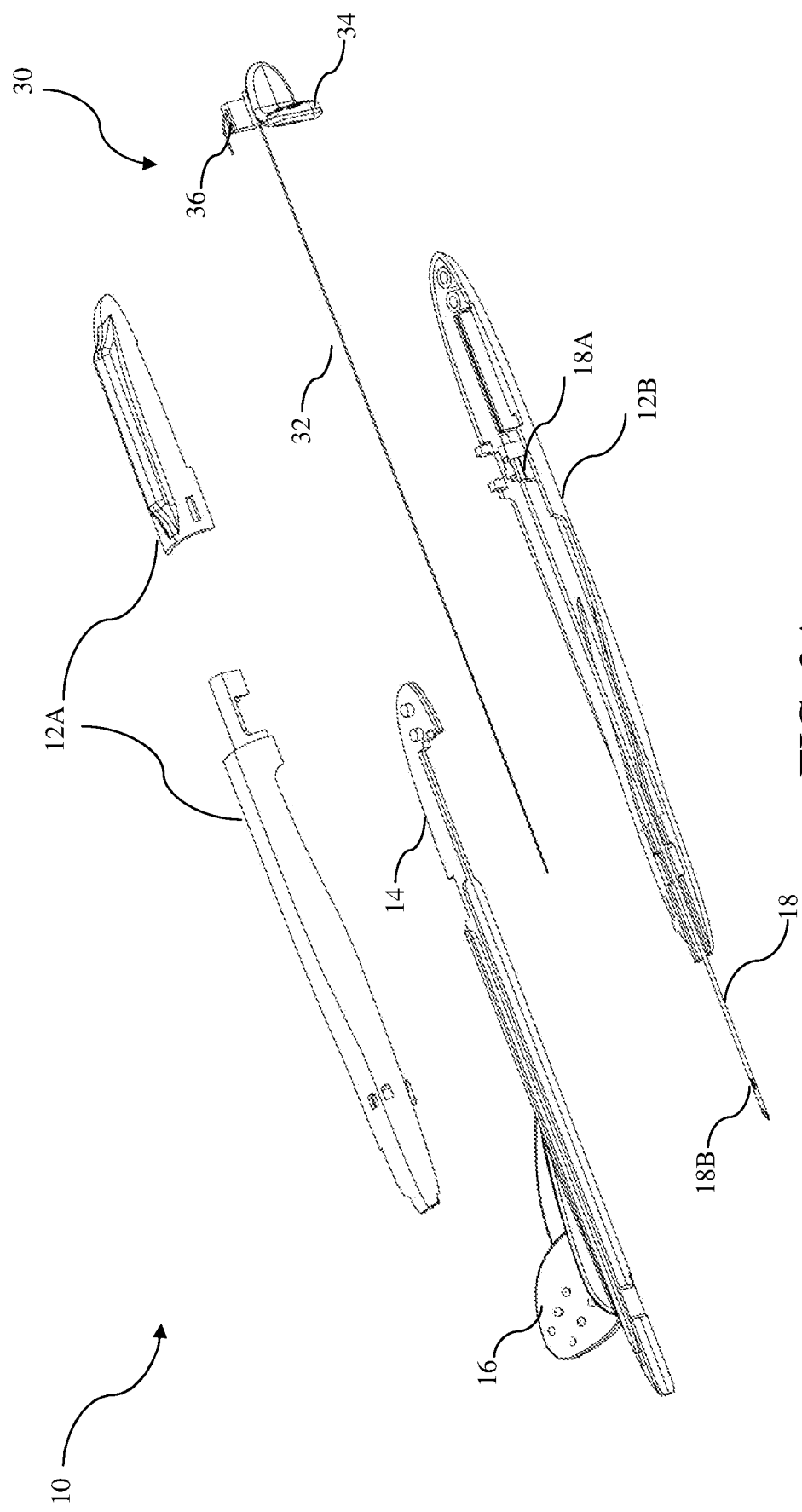
FIGS. 3A and 3B are various exploded views of the insertion tool of FIG. 1 and FIG. 2.
Figure 3B:
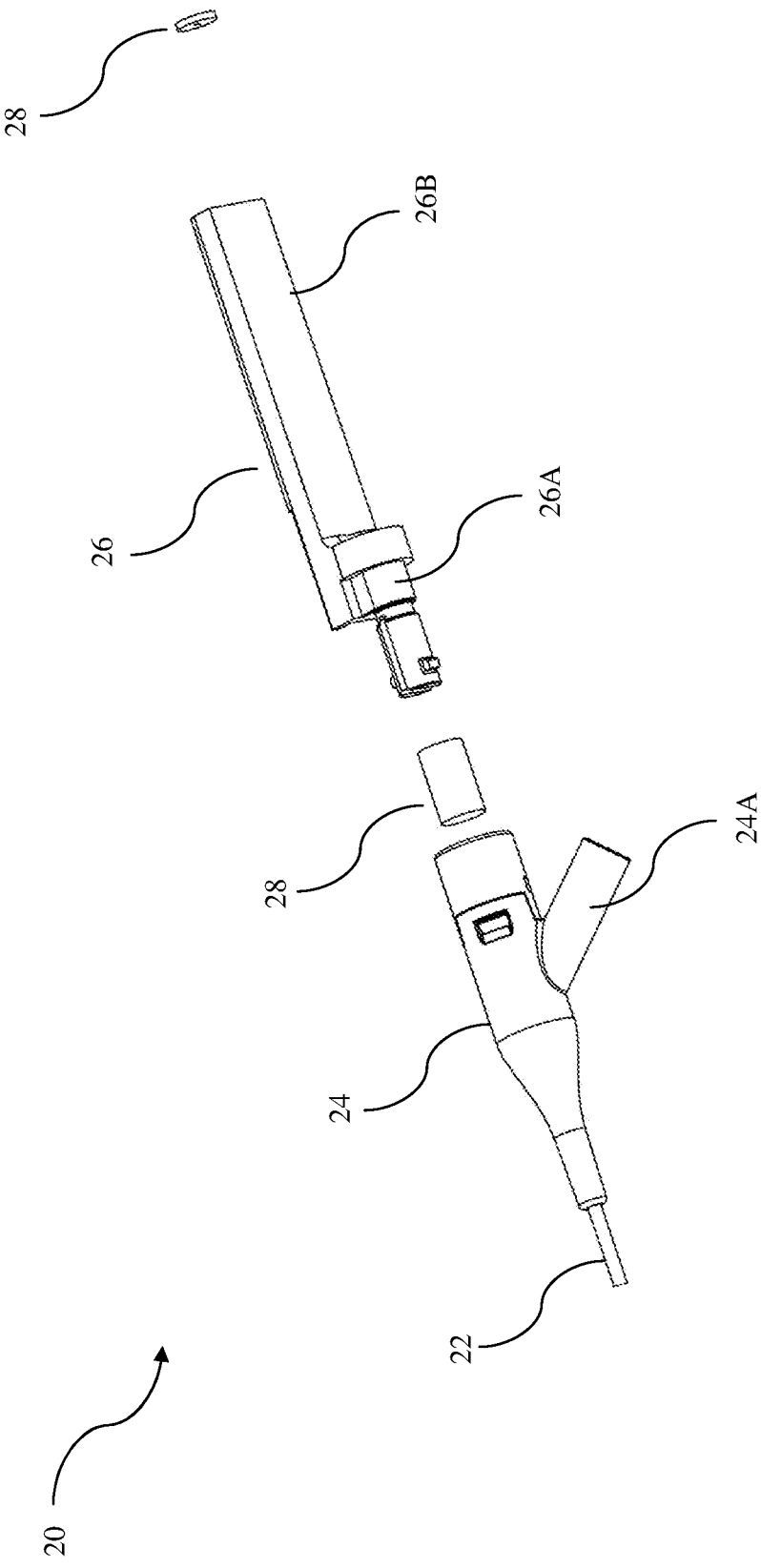

FIG. 3A and FIG. 3B are various exploded views of the insertion tool 10 of FIG. 1 and FIG. 2. Reference now is made to FIG. 3A, where a needle hub 18A supporting a hollow needle 18 is placed between the housing portions 12A and 12B. The needle 18 extends distally form the needle hub 18A, through the body of the insertion tool 10 and out of a distal end of the housing 12. In another embodiment, the needle 18 is at least partially hollow while still enabling the functionality described herein. In one embodiment, a notch 18B is defined through the wall of the needle 18 proximate the distal end thereof. The notch 18B enables flashback of blood to exit the lumen defined by the hollow needle 18 once access to the patient's vasculature is achieved during catheter insertion procedures. Thus, blood exiting the notch 18B can be viewed by a clinician to confirm that the needle is properly inserted into the vasculature.

As shown in FIGS. 2 and 3B, the insertion tool 10 further includes a catheter advancement assembly 20 for distally advancing a catheter 22 into the vasculature of the patient. The proximal end of the catheter 22 is connected to a catheter hub 24. Both of the catheter 22 and catheter hub 24 are initially disposed on the needle 18. And at least a portion of the catheter 22, and the catheter hub 24, are pre-disposed within the housing 12. In one embodiment, a distal portion of the catheter 22 extends out of the distal end of the housing 12. In one embodiment, the catheter hub 24 includes a handle extending out of the housing 12 from a slot 12C on the housing, and the handle of the catheter hub 24 can be used to effect the advancement of the catheter 22 and the catheter hub 24. The slot 12C exists between the first portion 12A and the second portion 12B of the housing 12, allowing the movement of the handle of the catheter hub 24. In another embodiment, the handle of the catheter hub 24 is a branch pipe 24A extending from the catheter hub 24. In another embodiment, a sterile protection is provided to the branch pipe.

Reference is continue made to FIGS. 2 and 3B, where the insertion tool 10 includes a safety cap 26. The safety cap 26 is initially attached to the catheter hub 24, and can be separated from the catheter hub 24 when it is distally slid to a certain position. In one embodiment, the safety cap 26 is locked to the housing 12 when sliding to the position. Details on this locking mechanism are to be described below.

In one embodiment, the safety cap 26 includes a first portion 26A wrapping the needle and a second portion 26B slidably attached to the rail 14. In one embodiment, the position where the catheter hub 24 and the safety cap 26 can be separated is a position where the tip of the needle 18 is isolated within the first portion 26A of the safety cap 26. In one embodiment, the second portion 26B of the safety cap 26 is locked to the rail 14 when the safety cap 26 slides to the position that the tip of the needle 18 is isolated within the first portion 26A of the safety cap 26. The locking between the safety cap 26 (more specifically the second portion 26B) and the rail 14 prevents the relative movement between the safety cap 26 and the needle 18, avoiding the re-exposure of the needle tip and thus eliminating the possibility that the needle pricks the clinician or the patient.

Referring to FIG. 3B, in one embodiment, the insertion tool 10 further includes at least one septum 28 to prevent blood exposure while the needle and catheter is inserted into or withdrawn from the body of the patient. There can be one or multiple septa placed inside the insertion tool 10. In one embodiment, a septum 28 (not shown in FIG. 3B) is disposed within the lumen of the catheter hub 24. In one embodiment, a septum 28 is disposed on the first portion 26A of the safety cap 26. In one embodiment, a septum 28 is disposed within the lumen of the first portion 26A of the safety cap 26. To be noted, a septum can also be disposed inside another element of the insertion tool, for example, the branch tube of the catheter hub 24. The size and shape of a septum is configured to fit the corresponding element or a lumen of the element, and when multiple septa are used the size and shape of each septa can be the same or different.

Referring back to FIG. 3A, in one embodiment, the insertion tool 10 comprises a guidewire advancement assembly 30 for distally advancing a guidewire 32 into, or withdrawing it from, the vasculature of the patient. In one embodiment, the guidewire advancement assembly 30 further includes a pusher 34 for operating the movement of the guidewire 32 in preparation for the advancement of the catheter 22.

In one embodiment, at least a portion of the guidewire 32 is disposed within the lumen of the needle 18. In an alternative embodiment, the distal end of the guidewire 32 is initially dispose within the tip of the needle 18, while the other end of the guidewire 32 is fixated to an anchor point on the housing 12 or the rail 14. The guidewire 32 proximally extends from the anchor point, enters a hole 36 disposed on the pusher 34 and is bended by the hole 36, extends away from the hole 36 and distally extends into the lumen of the needle 18. In one embodiment, the movement of the pusher 34 applies a friction force on the bended portion of the guidewire 32, so as to advance or retract the distal portion of the guidewire 32. When the pusher 34 is distally moved, the guidewire 32 is distally advanced over a distance two times the moving distance of the pusher 34. This conveniently increases the efficiency of guidewire advancement, which is desired in the operation of such a medical device.

Housing

Figure 4A:
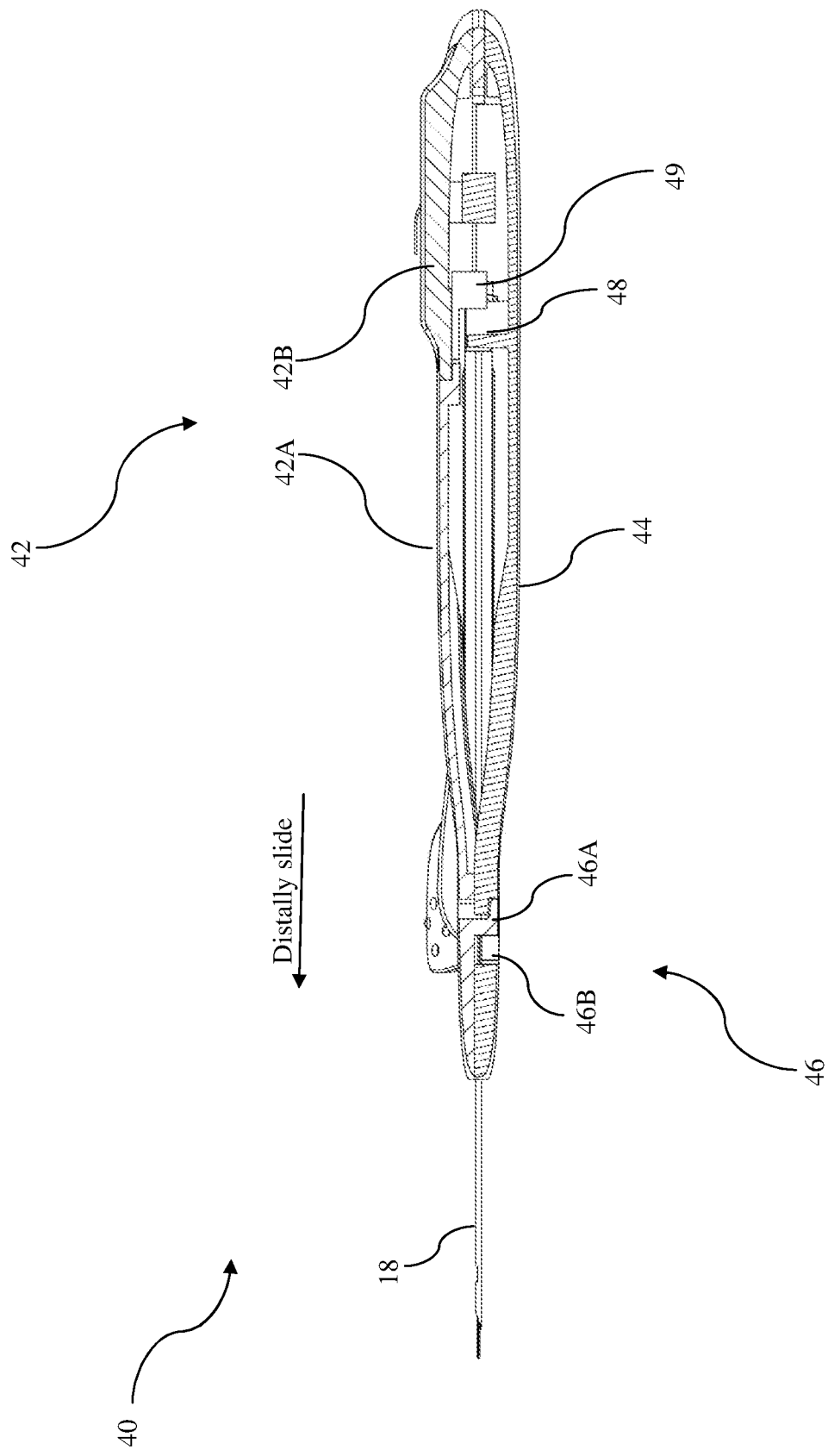
FIGS. 4A-4C are side views of a housing of the catheter insertion tool according to one embodiment of the present invention.
Figure 4B:
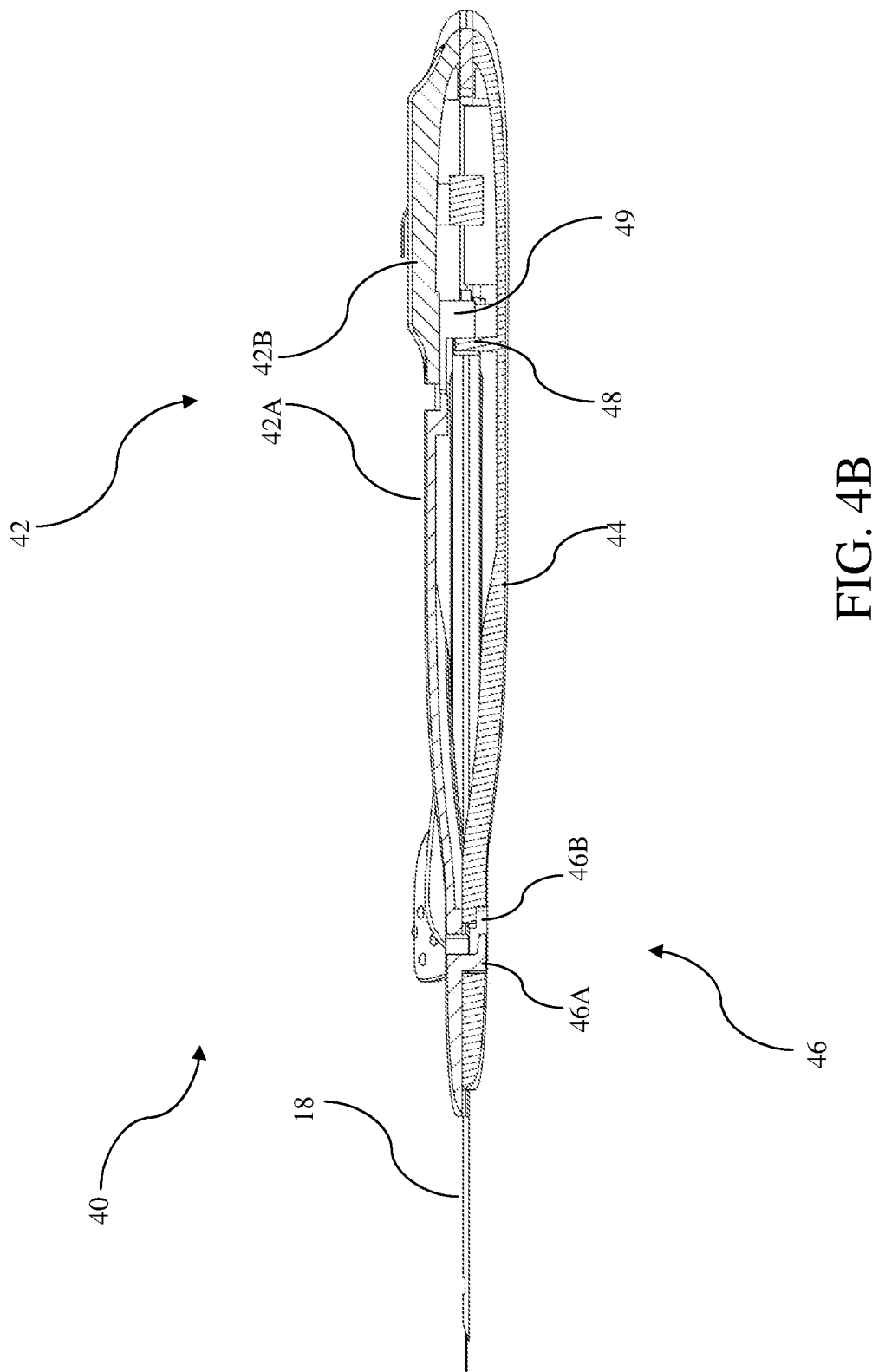

FIG. 4A and FIG. 4B are side views of a housing 40 of the catheter insertion tool of the present invention. The housing 40 includes a first portion 42 comprising a distal part 42A and a proximal part 42B, and a second portion 44 engaged with the first portion 42, wherein the distal part 42A of the first portion 42 is configured to be able to distally slide with respect to the second portion 44 to release the engagement 46 between the first portion 42 and the second portion 44.

In one embodiment, the proximal part 42B of the first portion 42 is fixated to the second portion 44. Alternatively, the proximal part 42B of the first portion 42 is engaged with the second portion 44 via a separable configuration, for example a snap-fit joint, pin joint, rivet joint, buckle and so on. A force above a threshold magnitude is required to release the separable engagement between the proximal part 42B of the first portion 42 and the second portion 44, so as to prevent accidental separation of the housing. In another embodiment, the proximal part 42B of the first portion 42 and the second portion 44 are inseparable from each other or form an integrated piece.

Figure 4C:
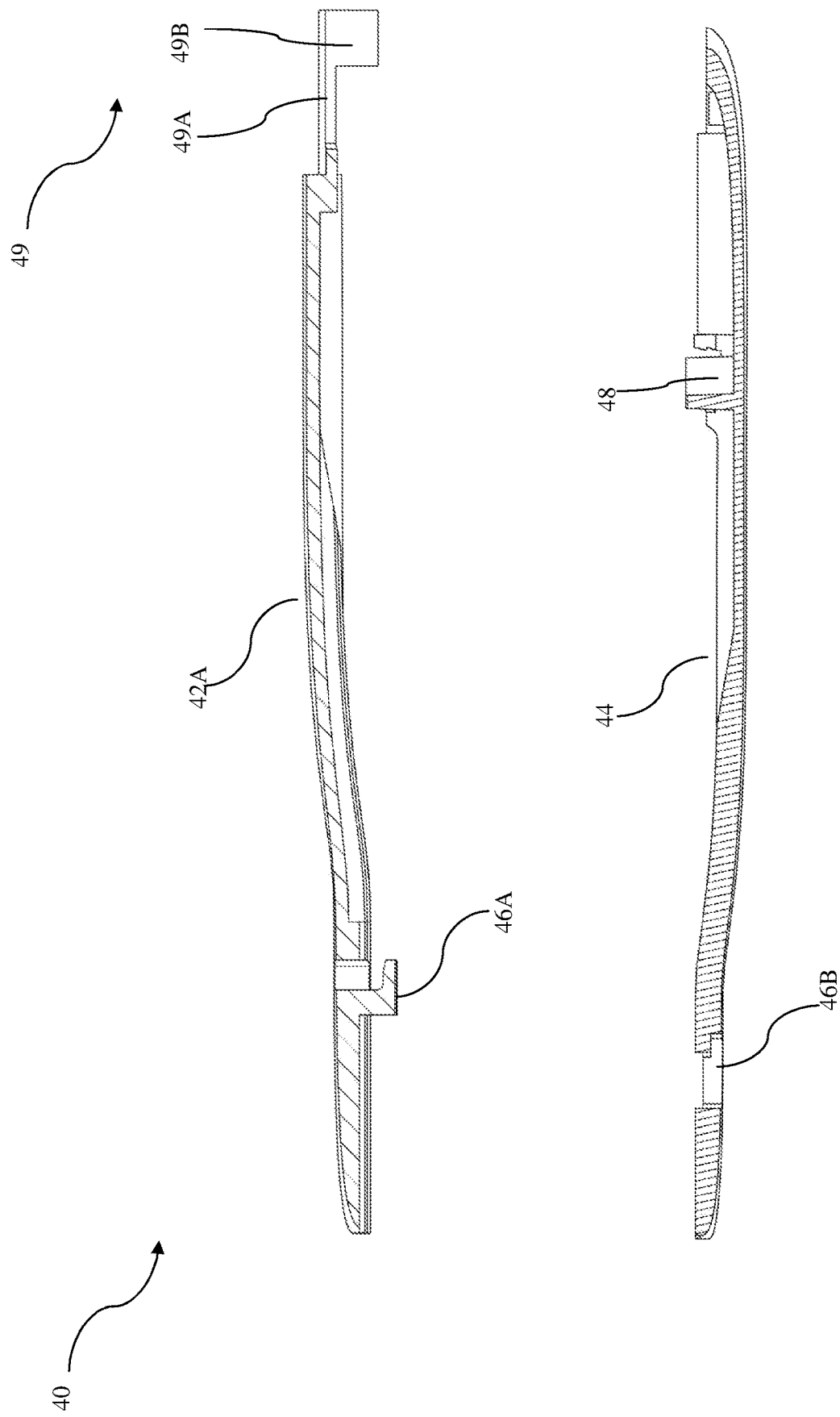
Figure 4D:
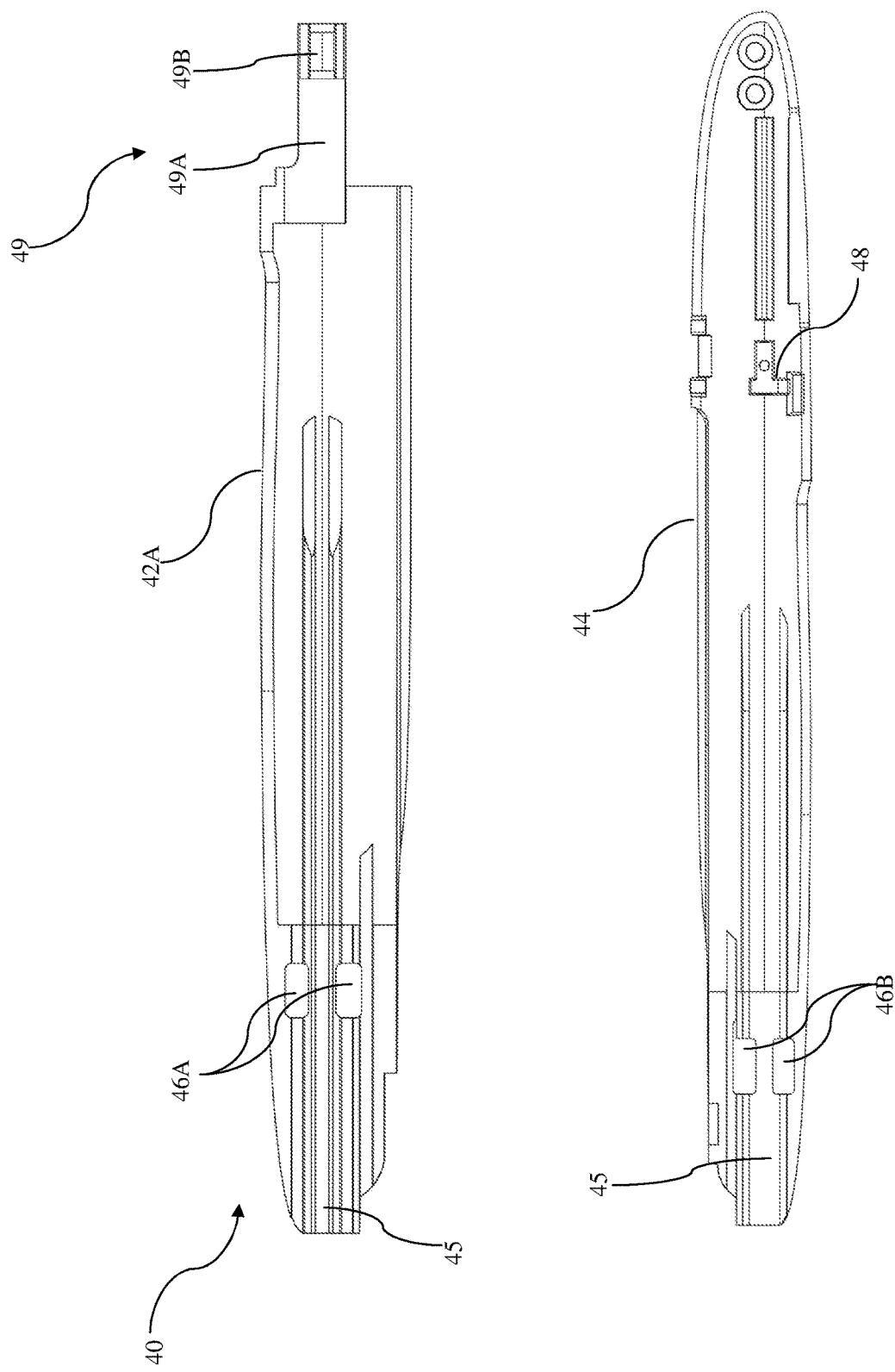
FIG. 4D shows the inner surface of the housing of FIGS. 4A-4C.

In one embodiment, as shown in FIG. 4C and FIG. 4D, a hook 46A is disposed on an inner surface of the distal part 42A of the first portion 42 of the housing. The hook 46A has a tip extending toward the proximal end of the housing 40. A slot 46B is disposed on the second portion 44. The slot 46B receives the hook 46A when the first portion 42 and the second portion 44 are engaged, and the hook 46A is released from the slot 46B when the distal part 42A of the first portion 42 is slide distally such that the first portion 42 is released from the second portion 44.

Refers back to FIG. 4A, the first portion 42 and the second portion 44 of the housing 40 are engaged with each other through the engagement 46 formed by the hook 46A and slot 46B and the engagement between the proximal part 42B of the first portion 42 and the second portion 44. In the direction pointed by the arrow, the distal part 42A of the first portion 42 can be distally slid with respect to the second portion 44 of the housing 40. The distal sliding of the distal part 42A of the first portion 42 results in the distal movement of the hook 46A with respect to the hole 46B. When the tip of the hook 46A reaches the position as shown in FIG. 4B, the hook 46A can be separated from the hole 46B, such that the engagement 46 is released and the distal part 42A of the first portion 42 and the second portion 44 can be separated in a perpendicular direction with respect to each other.

To be noted, while FIGS. 4A-4D only show one pair of hook 46A and hole 46B, in one embodiment, the housing 40 of the present invention includes two hooks and two holes. To better stabilize the engagement 46, as an optimal embodiment, two hooks are arranged in parallel on the inner surface of the distal part 42A and, correspondingly, two holes are arranged on the second portion 44 in the same way as the two hooks. Other numbers and arrangement of the hooks and the holes are possible and within the spirit of the present invention.

As shown in FIGS. 4A and 4B, in one embodiment, a base 48 is disposed on an inner surface of the second portion 44 of the housing 40 for holding the proximal end of a needle 18. The proximal end of the needle 18 is fixated to the hosing. In one embodiment, the base 48 includes a hole allowing the guidewire to extend into the lumen of the needle 18 via the hole.

As shown in FIG. 4D, in one embodiment, a groove 45 is disposed on an inner surface of at least one of the first and second portions 42/44, the groove 45 having an inner width which is wide enough to allow free movement of the catheter in an axial direction and narrow enough to restrict the movement of the catheter perpendicular to the axial direction. That is, the first and second portions of the housing when engaged with each other provides supporting for the distal portion of the needle 18 which limits the swing of the needle 18 while the needle 18 is being inserted into or withdrawn from a patient's body.

In one embodiment, the distal part 42A and the proximal part 42B are always connected to each other before or after the distal movement of the distal part 42A. The connection can be formed by an elastic, or foldable, or hinged connection. Examples of an elastic or foldable connection can be a hinge, spring or another flexible piece.

In another embodiment, the distal part 42A of the first portion 42 can be separated from the second portion 44 after the distal part is distally slid to release the engagement between the first portion 42 and the second portion 44.

Continually refer to FIGS. 4A-4D. In another embodiment, the proximal end of the distal part 42A of the first portion 42 includes a structure 49 which is clamped between the proximal part 42B of the first portion 42 and the second portion 44, movement of the structure 49 being limited within a cavity formed by the proximal part 42B of the first portion 42 and the second portion 44. Specifically, in one embodiment, the structure 49 includes a flexible sheet 49A extending proximally from the proximal end of the distal part 42A, and two walls 49B vertically extending from two sides of the end portion of the flexible sheet 49A. In one embodiment, after the distal part 42A is distally slid over a certain distance, the structure 49 is blocked by the base 48 so as to prevent further distal movement of the distal part 42A of the first portion 42. The certain distance is also the distal movement distance of the hook 46A that allows the hook 46A to be released from the hole 46.

In one embodiment, the sheet 49A and the two walls 49B of the structure 49 of the distal part 42A engage with a ridge extending from the base 48. The ridge acts like a rail for the structure 49, which allows a distal movement along the ridge, but also restricts the swing of the structure 49 during the distal movement.

In one embodiment, the structure 49 is clamped by the base 48 of the second portion 44 and the inner surface of the proximal part 42B of the first portion 42. This prevents the distal part 42A from being detached from the rest of the housing, and allows the open-close movement of the distal part 42A with respect the second portion 44 with an angle. Such a mechanism avoids the housing form falling apart after use, which is good for medical safety (for example, prevention of needle stick and/or blood contamination) and user experience.

Figure 5A:
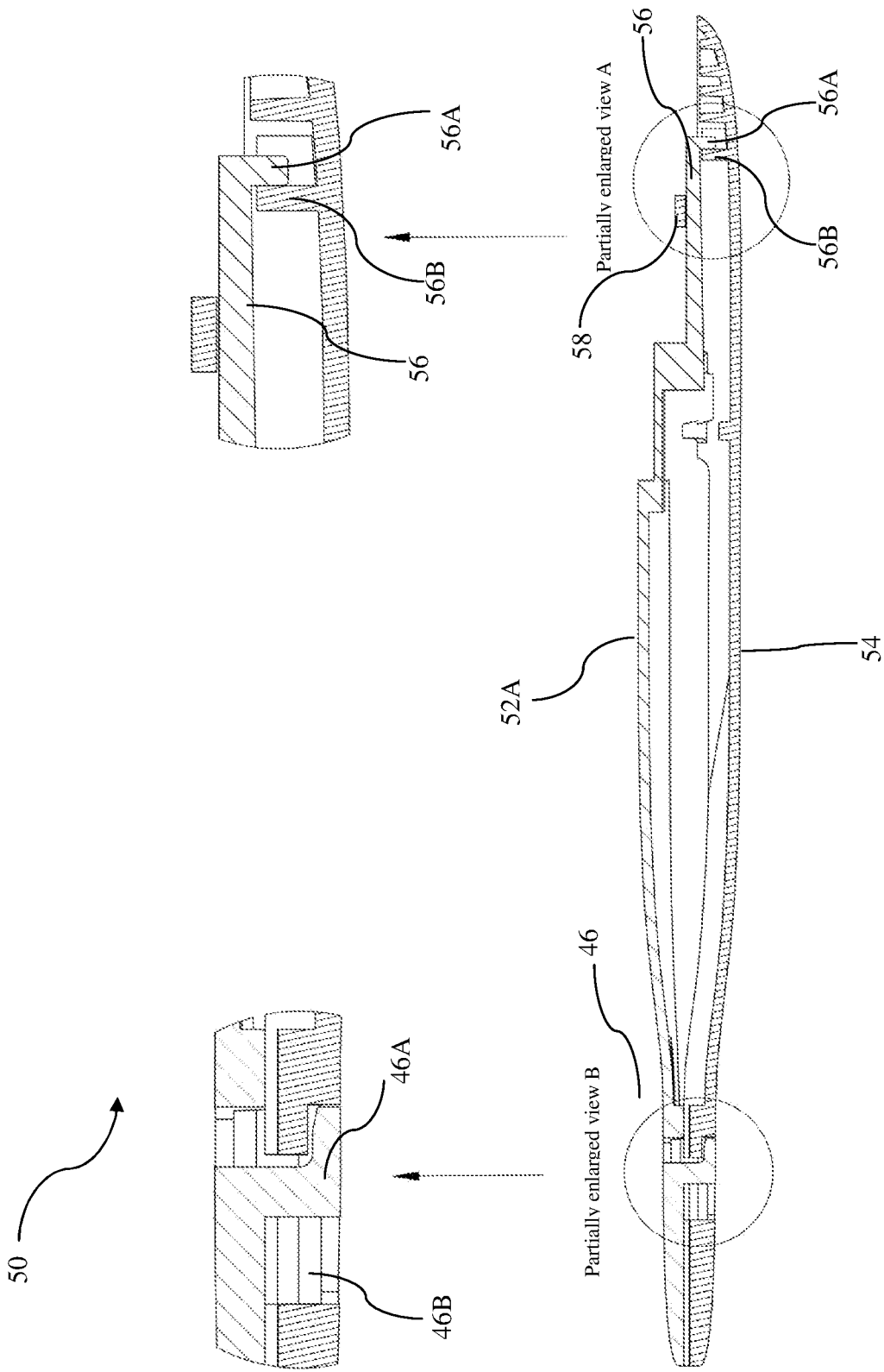
Figure 5B:
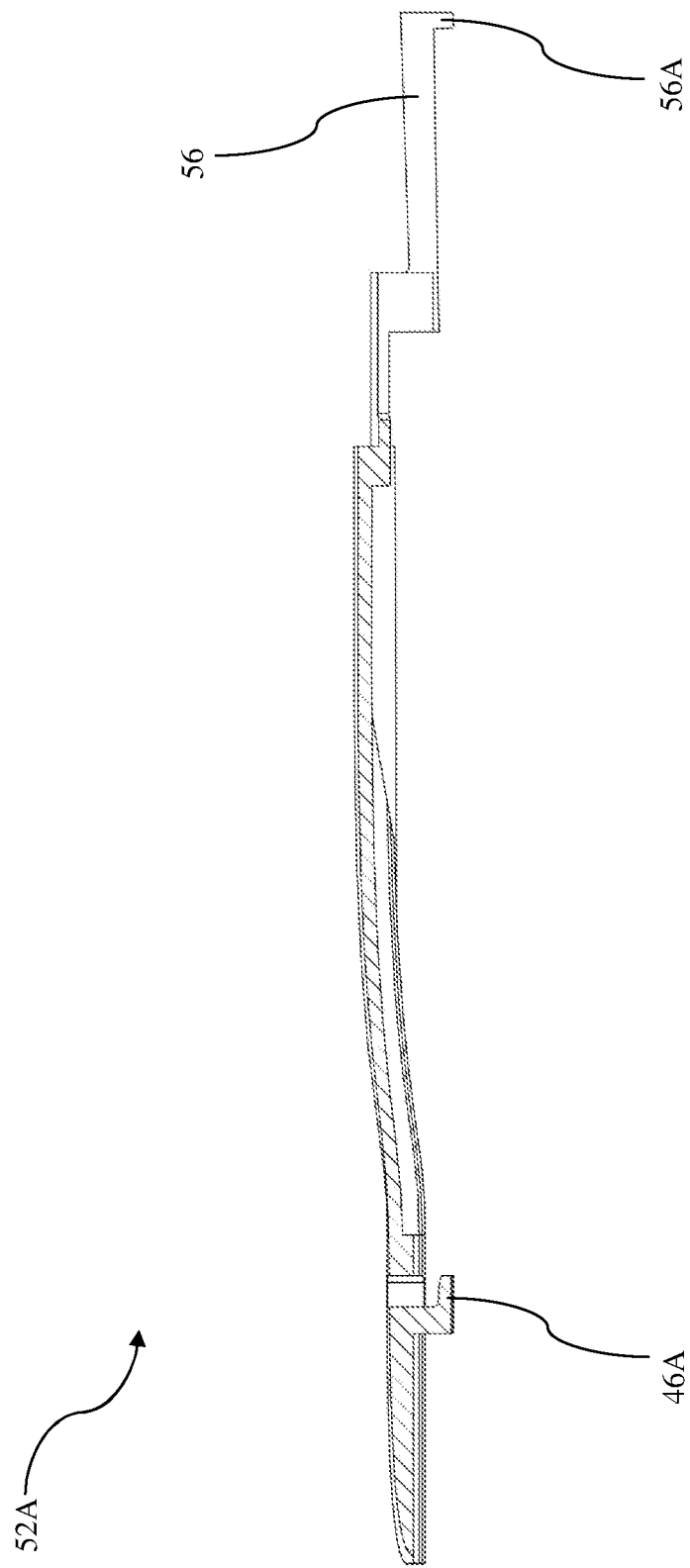

FIGS. 5A-5C are side views of a housing 50 of the catheter insertion tool of the present invention. As shown in FIG. 5A, the housing 50 includes a first portion 52 comprising a distal part 52A and a proximal part similar to the proximal part 42B shown in FIGS. 4A and 4B, and a second portion 54 engaged with the first portion 52. The proximal end 56 of the distal part 52A of the first portion 52 is configured to be able to be axially locked to the second portion 54, and the distal part 52A of the first portion 52 is configured to be able to distally slide with respect to the second portion 54 when the locking between the proximal end 56 of the distal part 52A of the first portion 52 and the second portion 54 is released, so as to release the engagement 46 between the first portion 52 and the second portion 54.

Reference continues to be made to FIG. 5A, where in one embodiment, as shown in the partially enlarged view "A", a first protrusion 56A extends from the proximal end 56 of the distal part 52A toward the second portion 54, and a second protrusion 56B extends from the second portion 54 toward the proximal end 56 of the distal part 52A of the first portion 52. In FIG. 5A, the proximal end 56 of the distal part 52A of the first portion 52 is flexible and is biased (by a slider 58 for example) toward the second portion 54, and the first protrusion 56A is proximal relative to the second protrusion 56B, whereby the proximal end 56 of the distal part 52A of the first portion 52 is axially locked to the second portion 54 such that the first portion 52 cannot be axially and distally moved relative to the second portion 54.

FIG. 5B is the side view of the distal part 52A of the first portion 52 of the housing shown in FIG. 5A. The proximal end 56 of the distal part 52A shown in FIG. 5B is in a natural, unbiased state, and it is in the form of a bevel slightly tilting upwards proximally. The bevel may have a consistent thickness. Alternatively the thickness of the bevel may gradually increase or decrease distally, with the least or greatest thickness reached at the location of the first protrusion 56A (without accounting for the height of the first protrusion 56A itself). The bevel having such a varying thickness may help change the amount of the force the slider 58 imposes on the bevel and the friction between the slider 58 and the bevel.

FIG. 5C is the side view of the housing 50 when the locking between the proximal end 56 of the distal part 52A of the first portion 52 and the second portion 54 is released. In one embodiment, when the slider 58 is moved distally, the force the slider 58 imposes on the proximal end 56 of the distal part 52A of the first portion 52 decreases and the proximal end 56 is gradually unbiased, and accordingly the first protrusion 56A moves upward relative to the second protrusion 56B. When the slider 58 is distally moved to a certain position as shown in FIG. 5C, the first protrusion 56A moves up to reach a position where the second protrusion 56B no longer blocks the distal movement of the first protrusion 56A and thus the locking between the proximal end 56 of the distal part 52A of the first portion 52 and the second portion 54 is released.

Figure 5D:
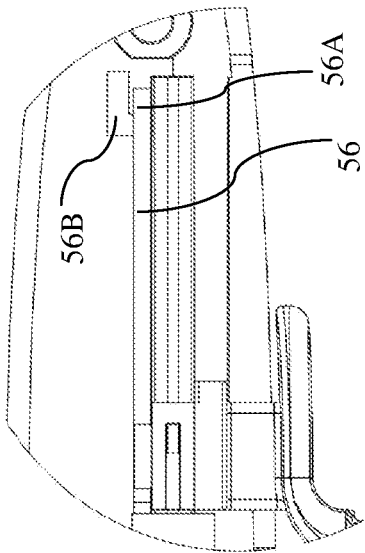
FIGS. 5D-5F show various views of the housing of FIGS. 5A-5C.
Figure 5D:
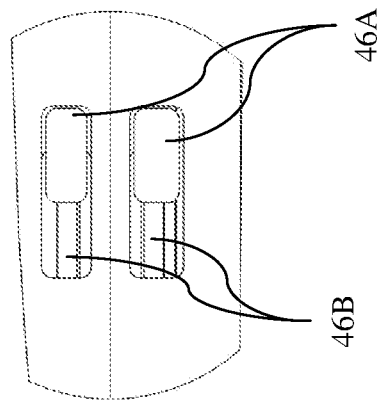
Figure 5D:
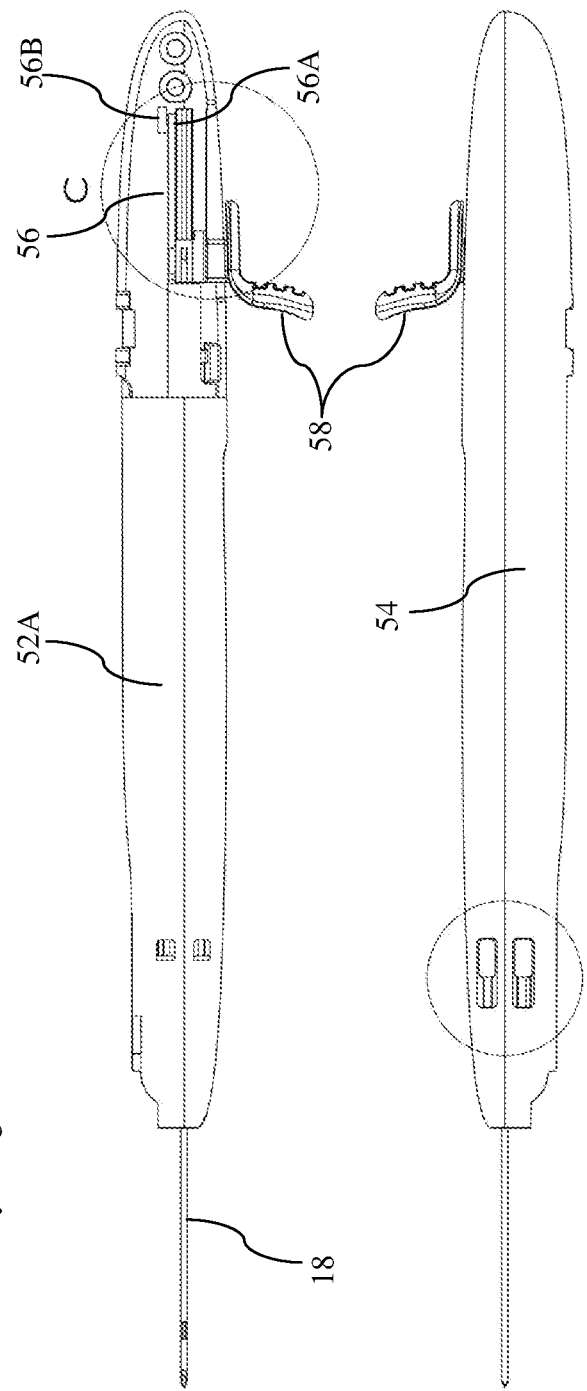
Figure 5E:
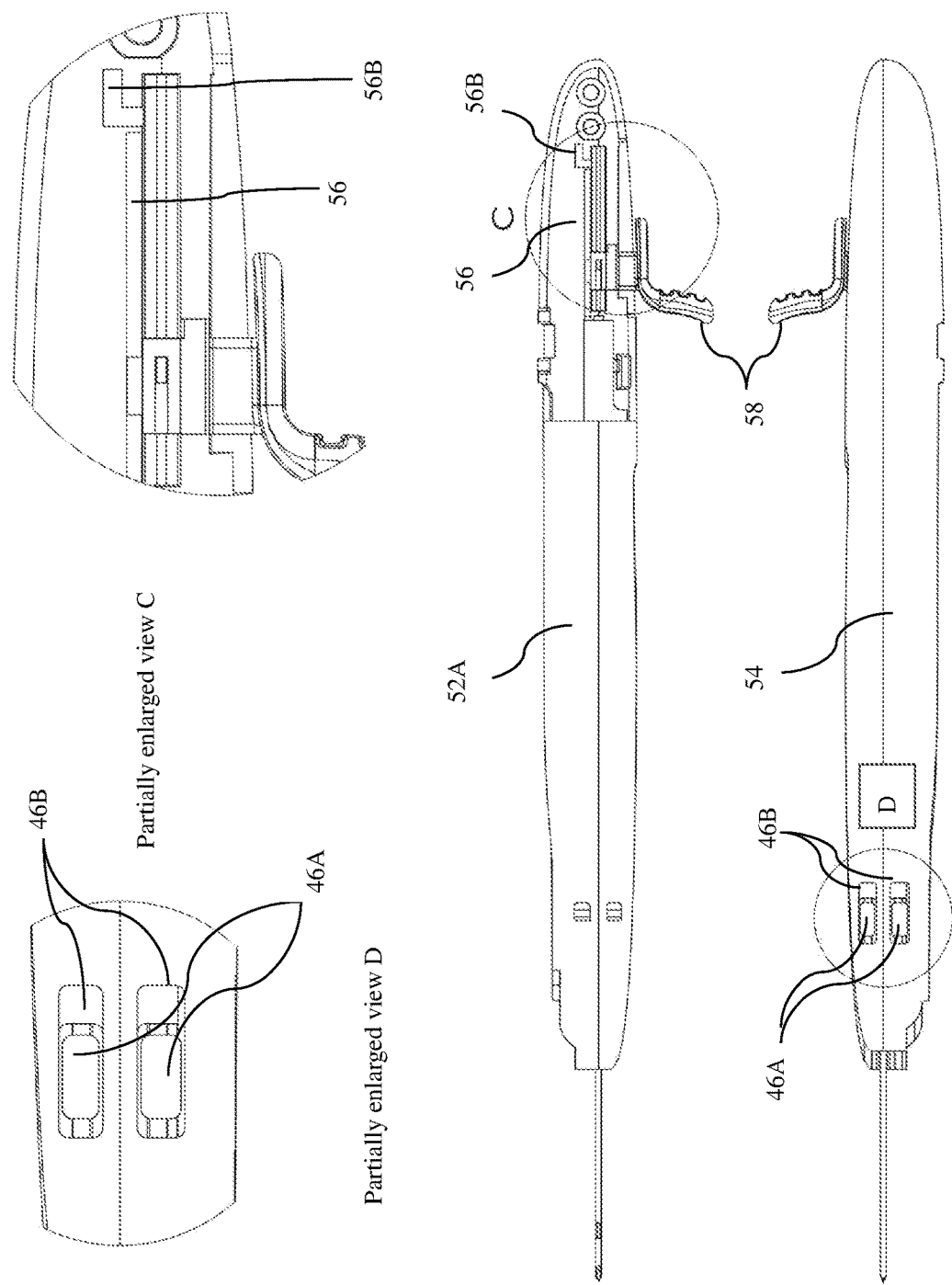
Figure 5F:
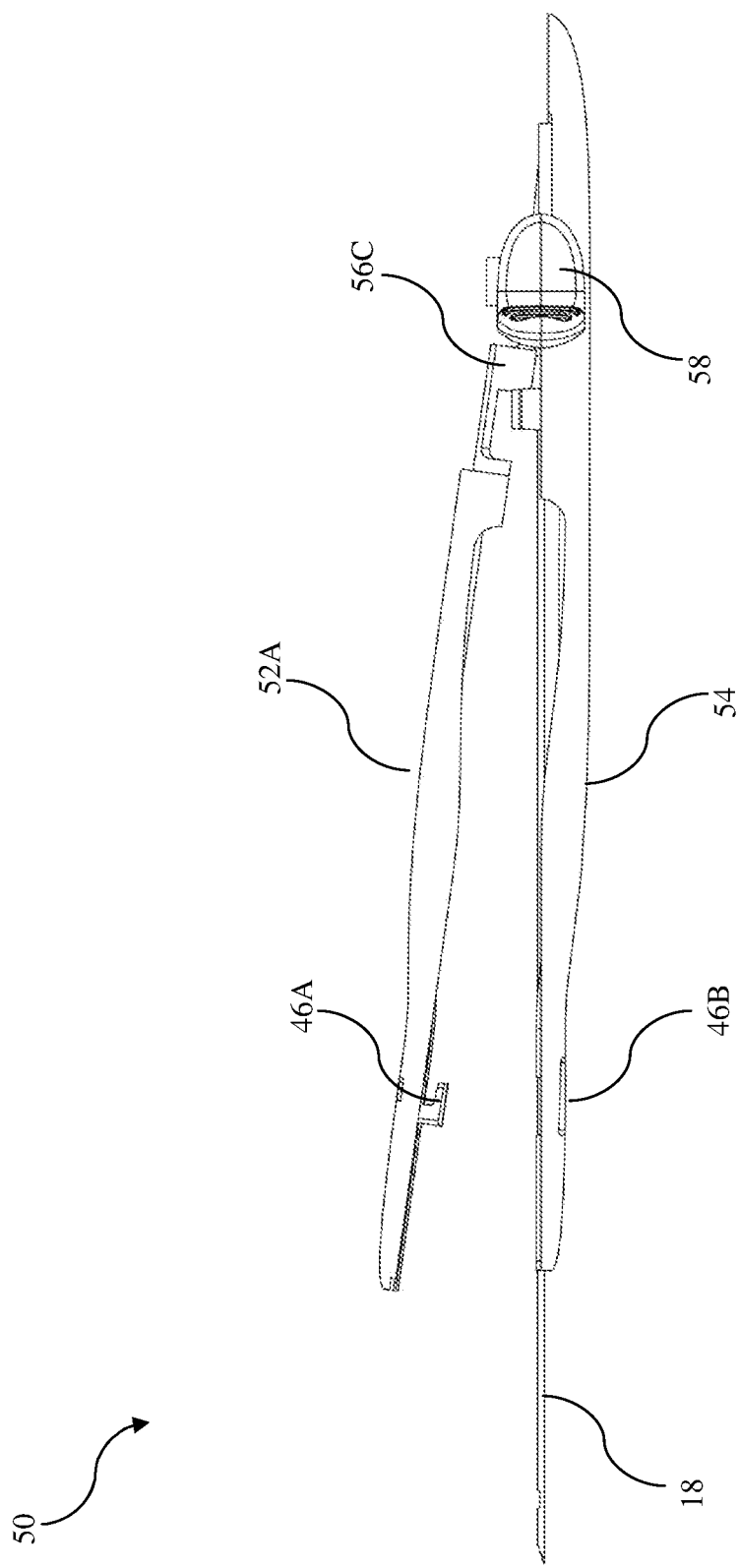

Similar to the housing 40 in FIGS. 4A-4D, in one embodiment as shown in FIGS. 5D and 5E, a hook 46A is disposed on an inner surface of the distal part 52A of the first portion 52 of the housing 50, and a slot 46B is disposed on the second portion 54 of the housing 50 in a position corresponding to the hook 46A. The hook 46A may be in a form of first perpendicularly protruding from the inner surface of the distal part 52A of the first portion 52 of the housing 50 and then extending horizontally and proximally, as shown in FIG. 5F. The slot 46B receives the hook 46A when the first portion 52 and the second portion 54 are engaged, and the hook 46A is released from the slot 46B when the locking between the proximal end 56 of the distal part 52A of the first portion 52 and the second portion 54 is released and the distal part 52A of the first portion 52 is slide distally, such that the first portion 52 can be released from the second portion 54.

FIG. 5F is the side view of the insertion tool showing the state when the engagement between the distal part 52A of the first portion 52 and the second portion 54 is released. In one embodiment, the proximal end 56 of the distal part 52A of the first portion 52 includes a structure 56C which is clamped between the proximal part (not shown in FIG. 5F) of the first portion 52 and the second portion 54, and movement of the structure 56C is limited within a cavity formed by the proximal part of the first portion 52 and the second portion 54. Specifically, in one embodiment, the structure 56C is similar to the structure 49 as shown in FIGS. 4A-C. In one embodiment, after the distal part 52A is distally slid over a certain distance, the structure 56C is blocked by the base 48 so as to prevent further distal movement of the distal part 52A of the first portion 52, wherein said certain distance is also the distal movement distance of the hook 46A that allows the hook 46A to be released from the slot 46B.

Such a locking mechanism between the proximal end 56 of the distal part 52A of the first portion 52 and the second portion 54 can effectively prevent a clinician's inadvertent operation which may cause distal movement of the distal part of the first portion of the housing and thus prevent unwanted separation of the housing. Additionally, in one embodiment, besides releasing the axial locking between the distal part 52A of the first portion 52 and the second portion 54, the distal movement of the slider 58 is also configured to advance the guidewire simultaneously, and such a configuration increases the operational efficiency and safety.

Needle Tip Protection

Figure 6A:
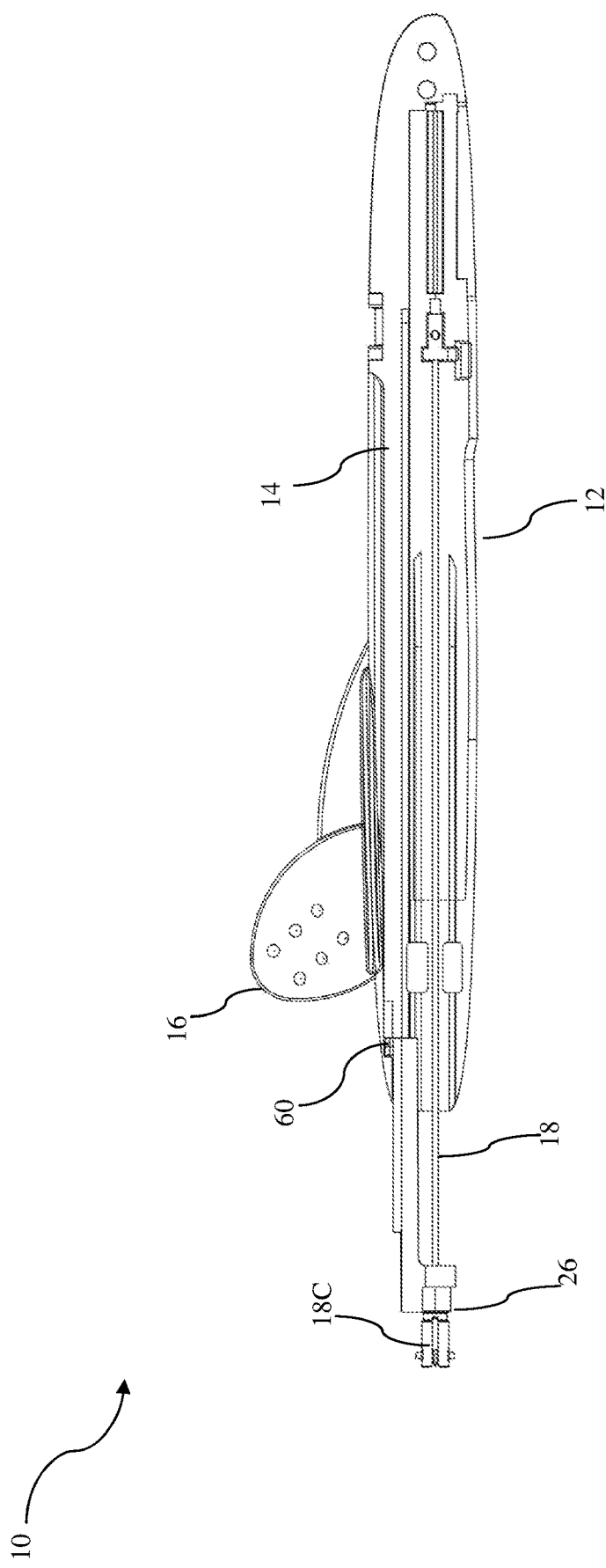
FIGS. 6A and 6B show various views of the inner structure of the insertion tool according to one embodiment of the present invention.

FIG. 2 and FIG. 6A shows the inner structure of one embodiment of the insertion tool 10 of the present invention. Specifically, FIG. 2 is a top view of the insertion tool 10 without the first portion 12A of the housing 12. In one embodiment, the insertion tool 10 of the present invention includes a housing 12, a rail 14 attached to the housing, a needle 18 distally extending from the housing 12, a catheter advancement assembly 20, a guidewire advancement assembly 30, wherein the catheter advancement assembly 20 includes a catheter 22, a catheter hub 24 and a safety cap 26 which is separably attached to the catheter hub 24.

Further to the status shown in FIG. 2, FIG. 6A shows the safety cap 26 distally sliding to a position where the safety cap 26 is locked to the rail 14. In one embodiment, the safety cap 26 is configured to be locked to the housing 12 when distally sliding to a position of isolating the tip of the needle 18 within the safety cap 26. To be noted, since the rail 14 can be a part of the housing or is attached to the housing, when the safety cap 26 is locked to the rail 14, the safety cap 26 can also be considered being locked to the housing 12. FIG. 6A clearly shows the position that the safety cap 26 is locked to the housing and the needle tip is isolated within the safety cap 26. At this position, the relevant movement between the safety cap 26 and the needle 18 is restricted, so as to prevent the re-exposure of the needle tip.

Figure 6B:
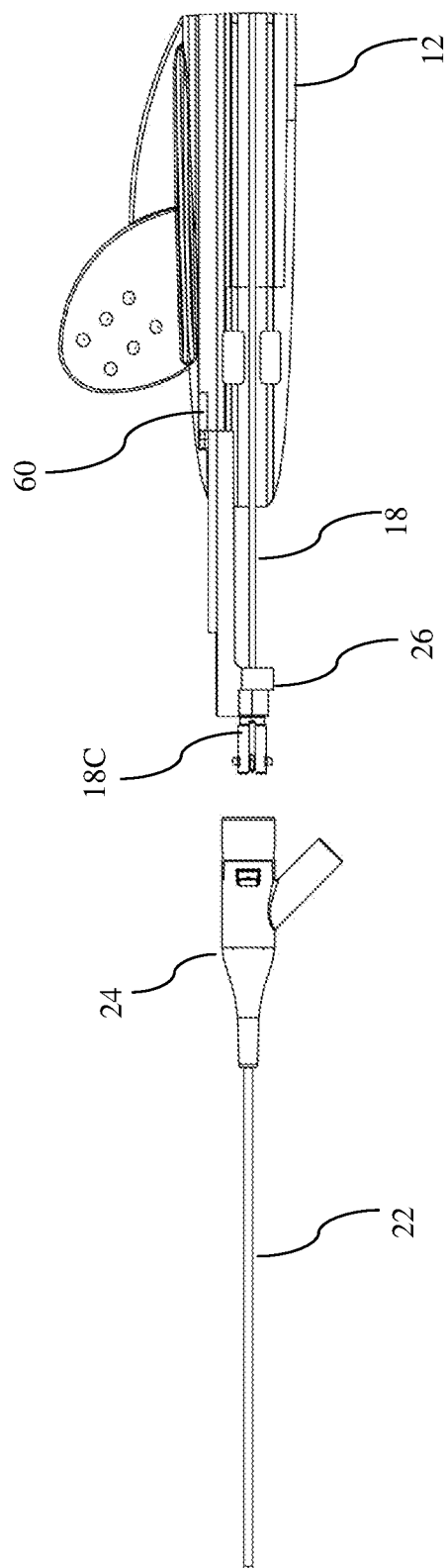

FIG. 6B shows the view that the catheter hub 24 is separated from the safety cap 26 when the safety cap 26 is at the position as described in FIG. 6A.

As shown in FIGS. 6A and 6B, in one embodiment, the safety cap 26 is locked to the housing 12 at a location 60 and the tip 18C of the needle 18 is isolated within the safety cap 26 when the safety cap 26 slides to the position of isolating the tip 18C of the needle within the safety cap.

Figure 6C:
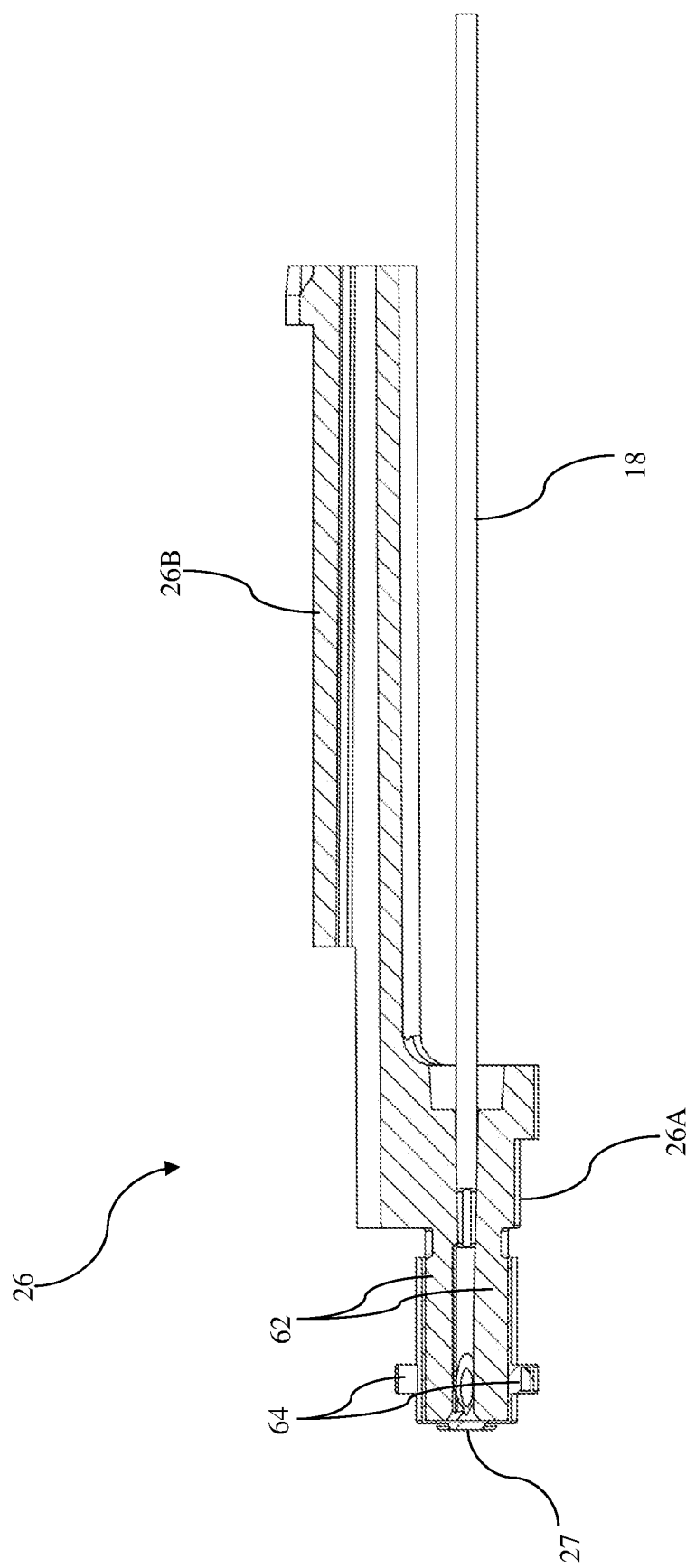
FIG. 6C shows the structure of a safety cap of the insertion tool according to one embodiment of the present invention.

FIG. 6C shows the structure of the safety cap 26 of one embodiment of the present invention. The safety cap 26 includes a first portion 26A and a second portion 26B. Viewed in combination with FIGS. 2, 6A and 6B, in one embodiment, the first portion 26A of the safety cap 26 wraps the needle 18 and the second portion 26B of the safety cap 26 is slidably attached to a rail 14. Specifically, in one embodiment, the first portion 26A of the safety cap 26 includes a lumen 27 extending through the first portion 26A which contains and wraps the needle 18.

In one embodiment, the first portion 26A of the safety cap 26 has two fingers 62. In one embodiment, the two fingers 62 have a slit between them which wraps the needle 18. In another embodiment, three, four or even more fingers are possible. In another embodiment, the fingers 62 are in the shape of a strip or column.

Figure 7A:
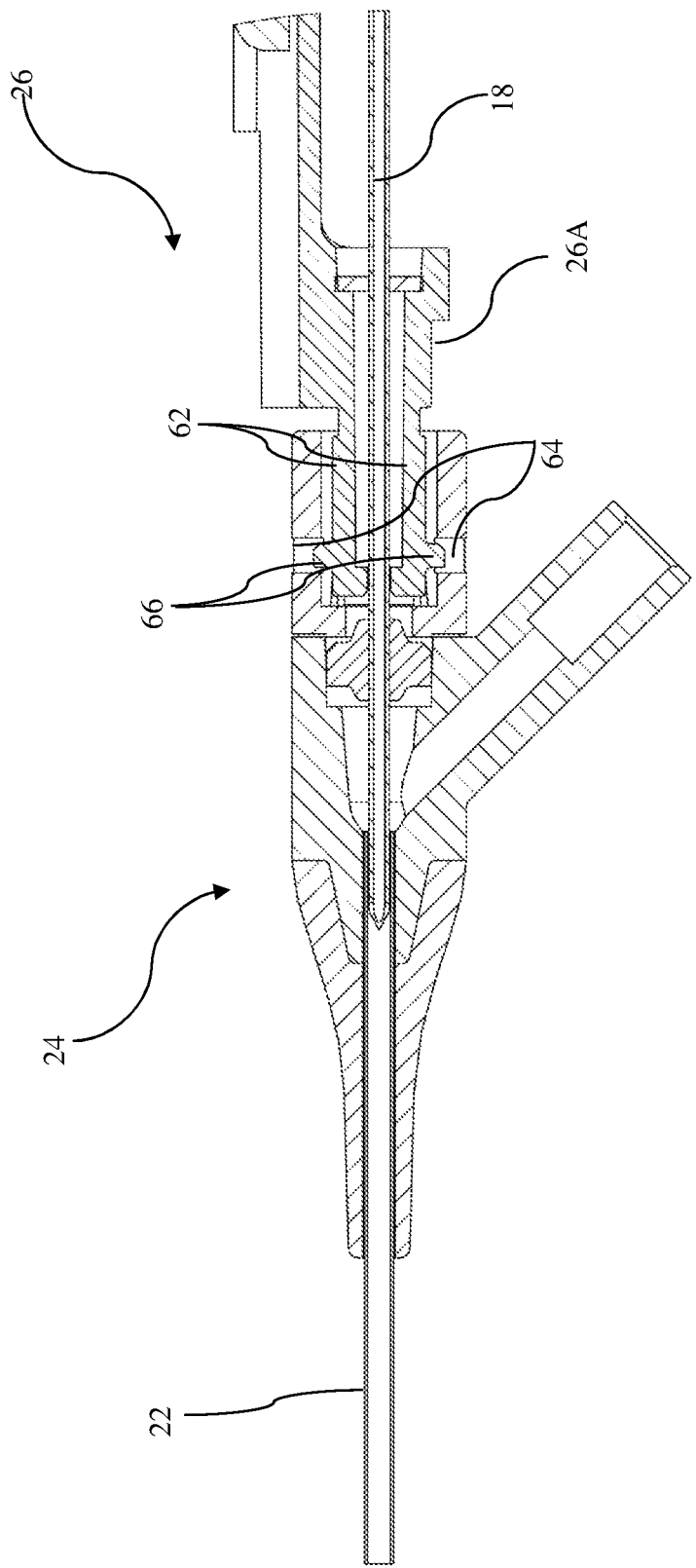
FIGS. 7A and 7B show the engagement between a catheter hub and a safety cap of the insertion tool according to one embodiment of the present invention.
Figure 7B:
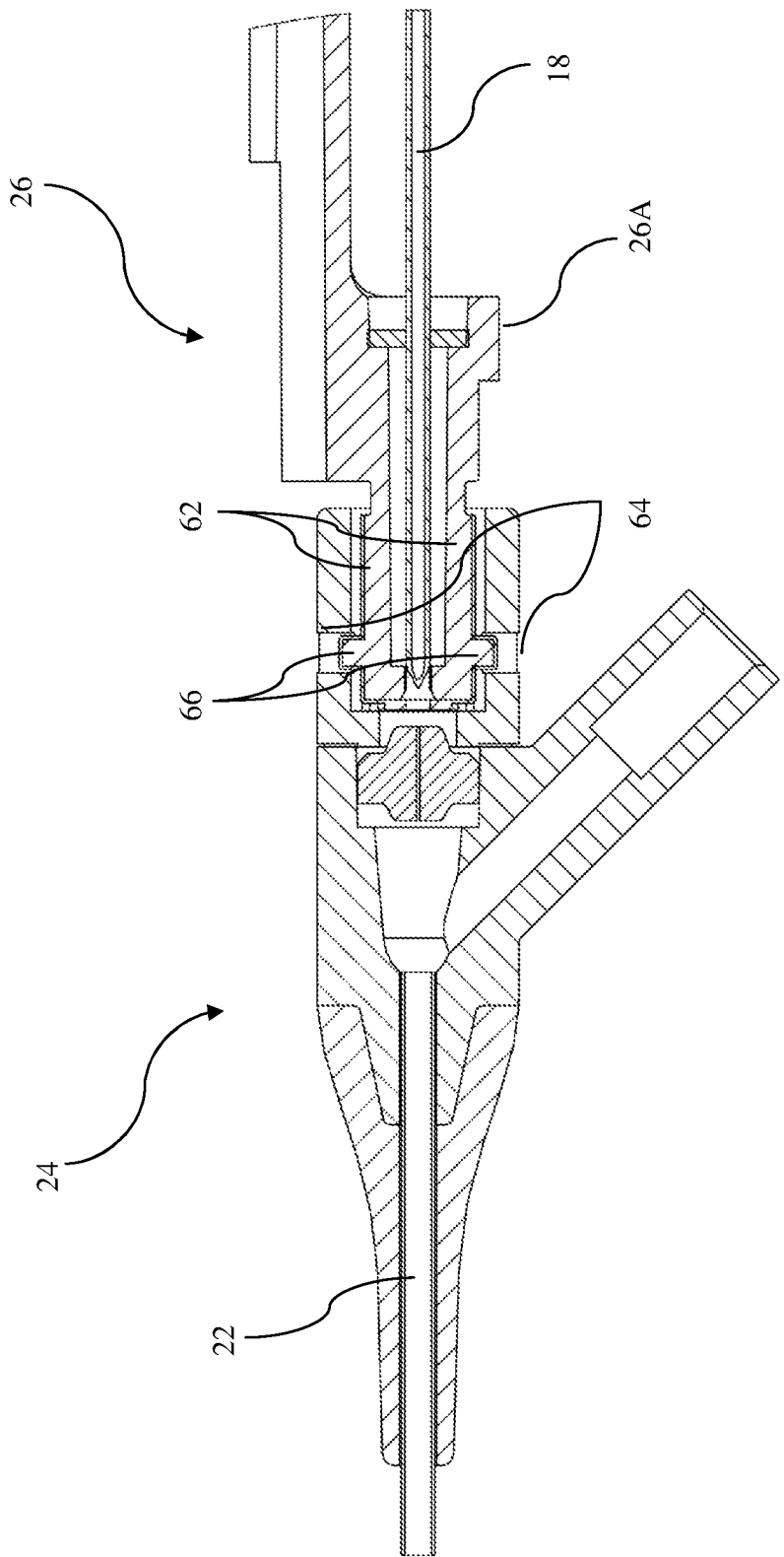

FIGS. 7A and 7B shows the engagement between the catheter hub 24 and the safety cap 26 of one embodiment of the present invention. The engagement is formed by inserting a protrusion 64 on the fingers 62 into a recess 66 disposed on the catheter hub 24.

Referring to FIG. 7A, in one embodiment, the fingers 62 are configured to be biased radially toward an inner surface of the catheter hub 24 when the stem of the needle 18 extends through the first portion 26A of the safety cap 26. That is, when the first portion 26A of the safety cap 26 wraps the needle stem, the fingers 62 are slightly biased/pressed outward by the needle 18. The radially biased fingers 62 insert their protrusion 64 into the recess 66, and the pressure from the needle 18 helps secure the insertion of the protrusion 64 into the recess 66, thus realizing the engagement between the catheter hub 24 and the safety cap 26.

Referring to FIG. 7B, in one embodiment, the fingers 62 are configured to be released from the biased position when the safety cap 24 distally slides to the position of isolating the tip of the needle 18. That is, when losing the pressure from the needle, the fingers 62 converge towards the axis of lumen of the catheter hub 24, and the protrusion 64 can be pulled out of the recess 66 and thus the catheter hub 24 can be separated from the safety cap 26.

Referring to FIG. 7A, in one embodiment, the fingers 62 are configured to remain in the same position when the stem of the needle extends through the first portion 26A of the safety cap 26 and when the safety cap 26 distally slides to the position of isolating the tip of the needle. That is, the fingers 62 are kept at the same position and basically are not biased with or without the pressure from the needle 18. And the outer diameter of the hollow cylinder formed by the fingers do not change whether the needle extends through the hollow cylinder or not. Nonetheless, the pressure from the needle 18 facilitates the insertion between the protrusion 64 and the recess 66.

Referring to FIG. 7B, in one embodiment, when losing the pressure from the needle, the fingers 62 are kept at the same position as biased/pressed by the needle 18. In this situation, when a user of the insertion tool tries to pull the safety cap 26 away from the catheter hub 24, the protrusion 64 is pulled out of the recess 66.

In one embodiment, each of the fingers 62 includes a protrusion 64, and a corresponding number of recesses 66 are disposed on the inner surface of the catheter hub. In one embodiment, each of the fingers 62 can include one or more protrusions 64.

Reference is now made to FIG. 6C. The proximal side of the protrusion 64 forms an obtuse angle relative to the surface of the finger 62 where the proximal side extends from the finger 62. That is, the proximal side of the protrusion 64 is a slope which allows the protrusion 64 to be pulled out from the recess 66 when the fingers 62 are not biased/pressed by the needle 18.

Figure 8A:
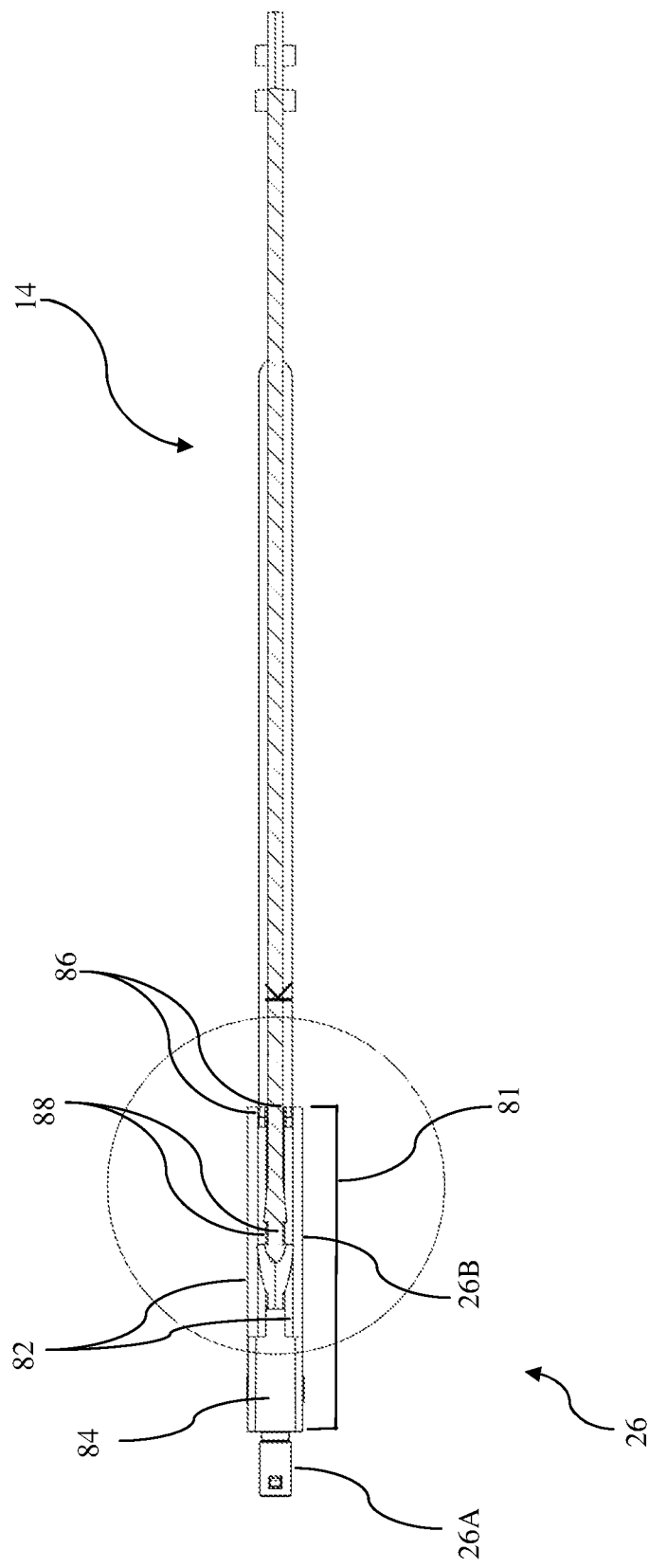
FIG. 8A is a top view of the cross section of a safety cap and a rail of the insertion tool according to one embodiment of the present invention.
Figure 8B:
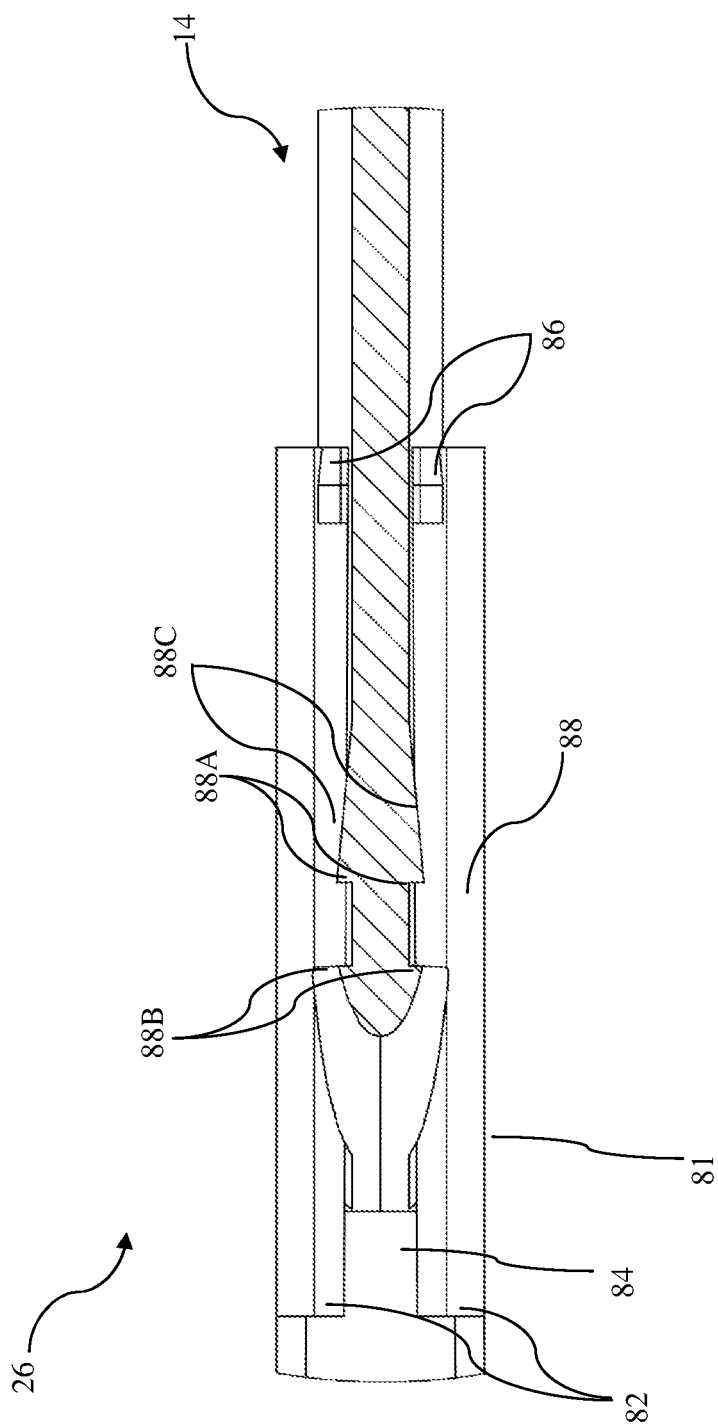
FIG. 8B is a partially enlarged view of FIG. 8A.
Figure 8C:
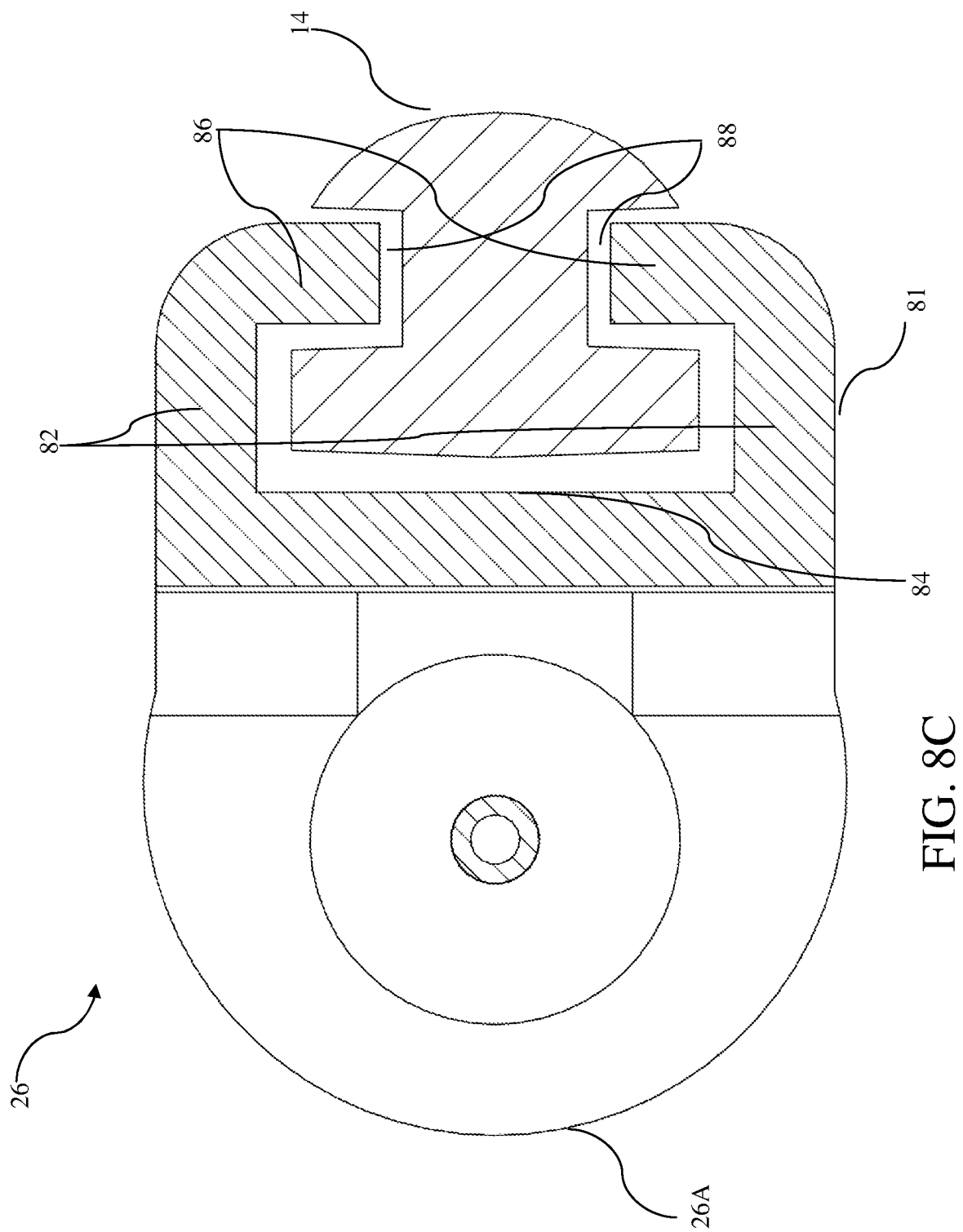
FIG. 8C is a cross section view of the safety cap of FIGS. 8A and 8B.

Referring to FIGS. 8A-C, the second portion 26B of the safety cap 26 is a lever 81, which slides along the rail 14. In one embodiment, the lever 81 includes two vertical walls 82 vertically extending from the two sides of a surface 84 of the lever 81 facing the rail 14. Each of the two vertical walls 82 has a horizontal part with a protrusion 86, which protrusion is locked within a notch 88 formed on the rail 14 so as to lock the safety cap 26 to the housing 12 when the safety cap 26 distally slides to the position of isolating the tip of the needle 18 within the safety cap 26.

To clearly depict the structure of the lever 81, reference is made to FIG. 8C, which is a sectional view of a plane perpendicular to the axis of the lumen of the safety cap 26. In one embodiment, the surface 84 of the lever facing the rail 14 includes two vertical walls 82, and the lever 81 is connected to the first portion 26A of the safety cap 26 on the opposite side of the surface 84. Each of the two vertical walls 82 has a horizontal part with a protrusion 86. Here the horizontal part is basically parallel to the surface 84, and in one embodiment, the vertical walls 82 extends throughout the full length of the lever, and the horizontal part is shorter than the full length of the lever. In another embodiment, the vertical walls 82 extend over only a partial length of the lever, and the horizontal part is shorter than the length of the vertical walls 82.

As shown in FIG. 8B, in one embodiment, the notch 88 is formed between two prominent bumps 88A and 88B disposed on the rail. In another embodiment, the proximal bump 88A has an inclined slope 88C at the proximal side and is substantially vertical to the surface of the rail at the distal side. In one embodiment, the distal bump 88B is raised higher from the surface of the rail 14 than the proximal bump 88A. While the protrusions 86 slide over the inclined slope 88C of the proximal bump 88A, the distance between the two protrusions 86 of the lever increases along the inclined slope 88C and the tension between the two protrusions 86 also gradually increases. When the protrusions 86 fall into the notch formed by the prominent bumps 88A and 88B, further movement of the protrusions 86 is blocked by the proximal side of the prominent bump 88B and distal side of the prominent bump 88A, and thus the safety cap 26 is locked to the rail 14.

In one embodiment, a user of the insertion tool (e.g. a clinician) feels a tactile sensation when the safety cap 26 is locked to the housing 12, for example when the protrusions 86 of the lever fall into the notch 88. In one embodiment, an audible sound is produced besides the tactile sensation.

Septum

Figure 9:
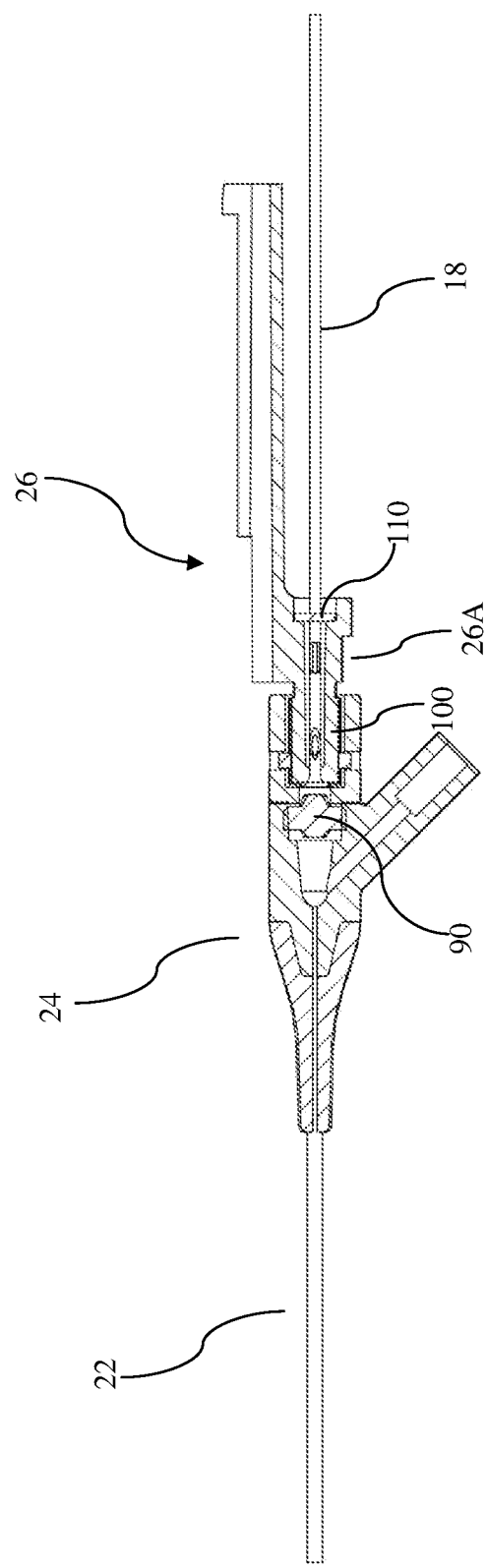
FIG. 9 shows septa disposed in the insertion tool according to one embodiment of the present invention.

Referring to FIG. 9, in one embodiment, the insertion tool includes at least one septum 90 to prevent blood exposure while the needle is inserted and the catheter is advanced into or away from the body of the patient. In one embodiment, the septum 90 can be disposed in a lumen within the insertion tool. For example, the septum 90 can be placed in a lumen of the catheter hub 24 of the insertion tool, and/or can be placed in a lumen of the safety cap 26 of the insertion tool.

In one embodiment, a septum 90 is disposed within the lumen of the catheter hub 24. In one embodiment, a septum 100 is disposed in the first portion 26A of the safety cap 26. In one embodiment, a septum 110 is disposed within the lumen of the first portion 26A of the safety cap 26. To be noticed, the septum can also be disposed in other element of the insertion tool, for example, the branch tube of the catheter hub 24. The size and shape of the septum 26 is configured to fit the corresponding element or lumen of the element, and the size and shape of each septa can be the same or different.

Figure 10A:
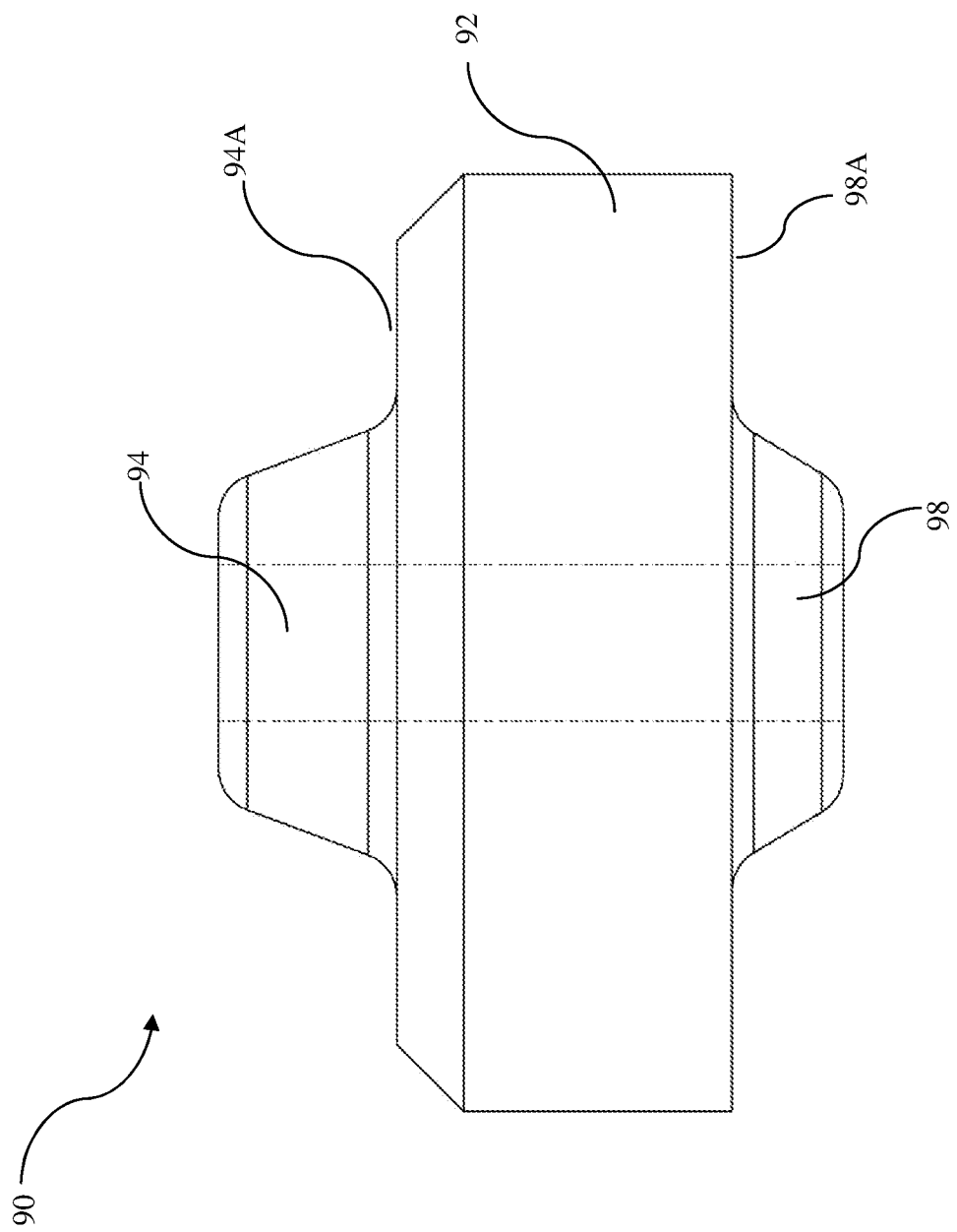
FIGS. 10A-10D show various views of a septum according to one embodiment of the present invention.

FIGS. 10A-D shows a septum 90 of one embodiment of the present invention. Referring to FIG. 10A, in one embodiment, the septum 90 comprises a cylindrical main body 92, and a first protrusion 94 which extends from a central portion of a top surface 94A of the main body 92. In one embodiment, the thickness of the cylindrical main body 92 is configured to be smaller than the distance between the tip and the notch of the needle 18, so as to reduce the friction between the septum 90 and the needle 18.

Figure 10B:
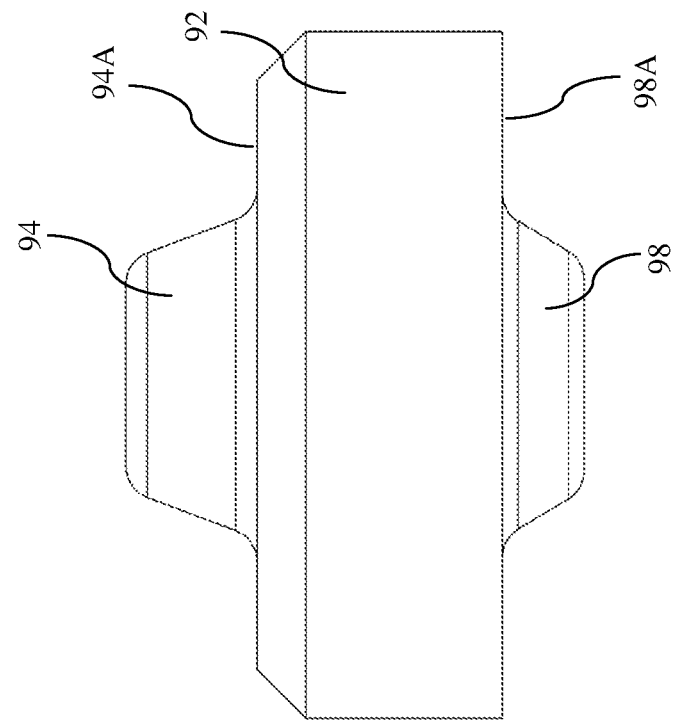
Figure 10B:
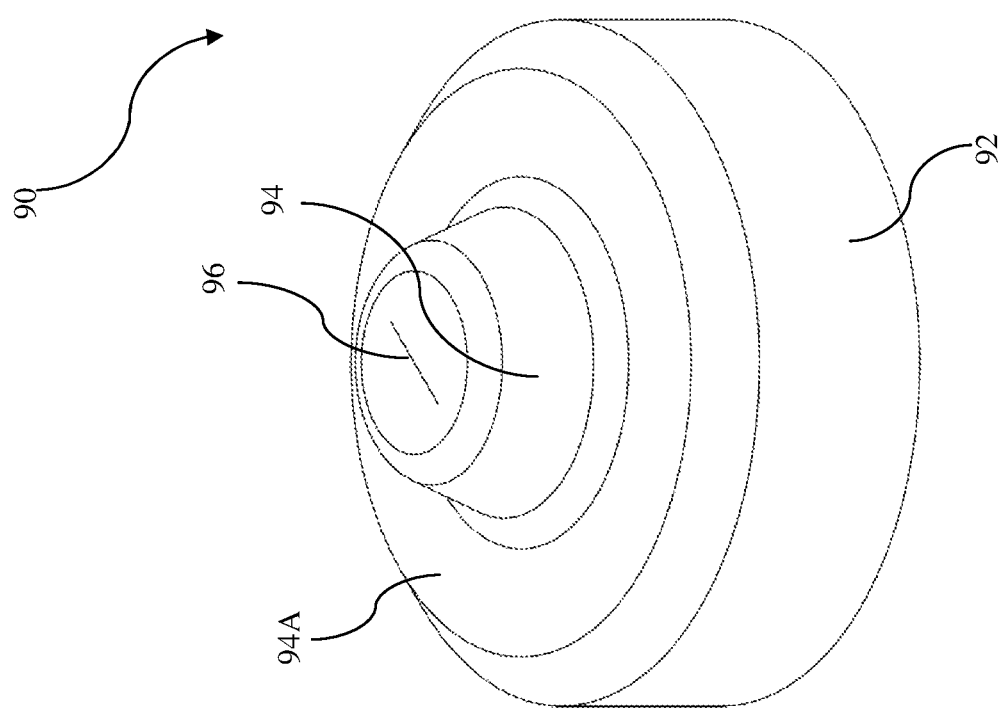

As shown in FIG. 10B, the septum 90 has a slit 96 formed within the septum 90 along the longitudinal axis of the septum. In one embodiment, the slit 96 is formed within the first protrusion. In one embodiment, the slit 96 extends through the septum. Specifically, the slit 96 can extend partially or entirely through the cylindrical main body 92 and the protrusion. In one embodiment, the slit 96 is enlarged when a needle 18 extends through it and is closed when the needle 18 is withdrawn from the septum 90. When the needle punctures the entire septum, the slit 96 consequentially extends throughout the septum. As a preferred embodiment, to ensure the sealing performance of the septum 90, the slit 96 initially is not through the entire thickness of the septum 90, and thus when the needle punctures the septum 90 during the assembling process, the septum 90 will tightly wrap the needle and provide a tight seal around the needle. As another embodiment, the septum 90 is formed without a through slit, and when the needle punctures the septum 90, the septum 90 tightly wraps the needle and may provide a tighter seal around the needle than a configuration with a slit does (assuming the configuration is the same in all the other aspects).

In one embodiment, the outer diameter of the main body 92 of the septum 90 is slightly larger than the inner diameter of the lumen of the catheter insertion tool before the septum 90 is installed in the lumen. Specifically, the outer diameter of the main body 92 of the septum 90 is larger than the inner diameter of the catheter hub 24. When the septum 90 is assembled in the lumen of the catheter hub 24, the inner surface of the catheter hub 24 is in tight contact with the septum 90 and thus provides better sealing.

In one embodiment, the first protrusion 94 of the septum is in the form of a circular truncated cone tapering from the top surface 94A of the main body 92 as shown in FIG. 10B. And the circular truncated cone is coaxial with the main body 92. In one embodiment, the first protrusion 94 is integral with the main body 92.

In one embodiment, the top surface 94A of the septum 90 is rounded at the peripheral. In one embodiment, the top surface of the circular truncated cone is rounded at the peripheral.

In one embodiment, the septum 90 of the present invention further includes a second protrusion 98 which extends from a central portion of the bottom surface 98A of the main body 92 opposite to the top surface 94A.

In one embodiment, the second protrusion 98 is in the form of a circular truncated cone tapering from the bottom surface 98A as shown in FIGS. 9A and 9B. And the circular truncated cone is coaxial with the main body 92. In one embodiment, the second protrusion 98 is integral with the main body 92 and forms an integrated body. In another embodiment, the second protrusion 98 is in the form of a cylinder embedded in the central of the main body 92. In another embodiment, the first protrusion 94 and the second protrusion 98 forms a cylinder embedded in the central of the main body 92. In one embodiment, the slit 96 partially extends in the cylinder formed by the first protrusion 94 or the second protrusion 98. In another embodiment, the slit 96 extends throughout the cylinder.

In one embodiment, the first and the second protrusion are the same in size and shape. In another embodiment, the second protrusion 98 is lower than the first protrusion 94. When the lumen of the catheter hub 24 is full of fluid (e.g. blood) at a side of the septum 90, the side surface of the first or the second protrusion facing the fluid assumes the centripetal pressure from the fluid and wraps the needle more tightly when a needle extends through the septum or shuts the slit more tightly if a slit has been formed through the septum, thus providing better fluid sealing.

Figure 10C:
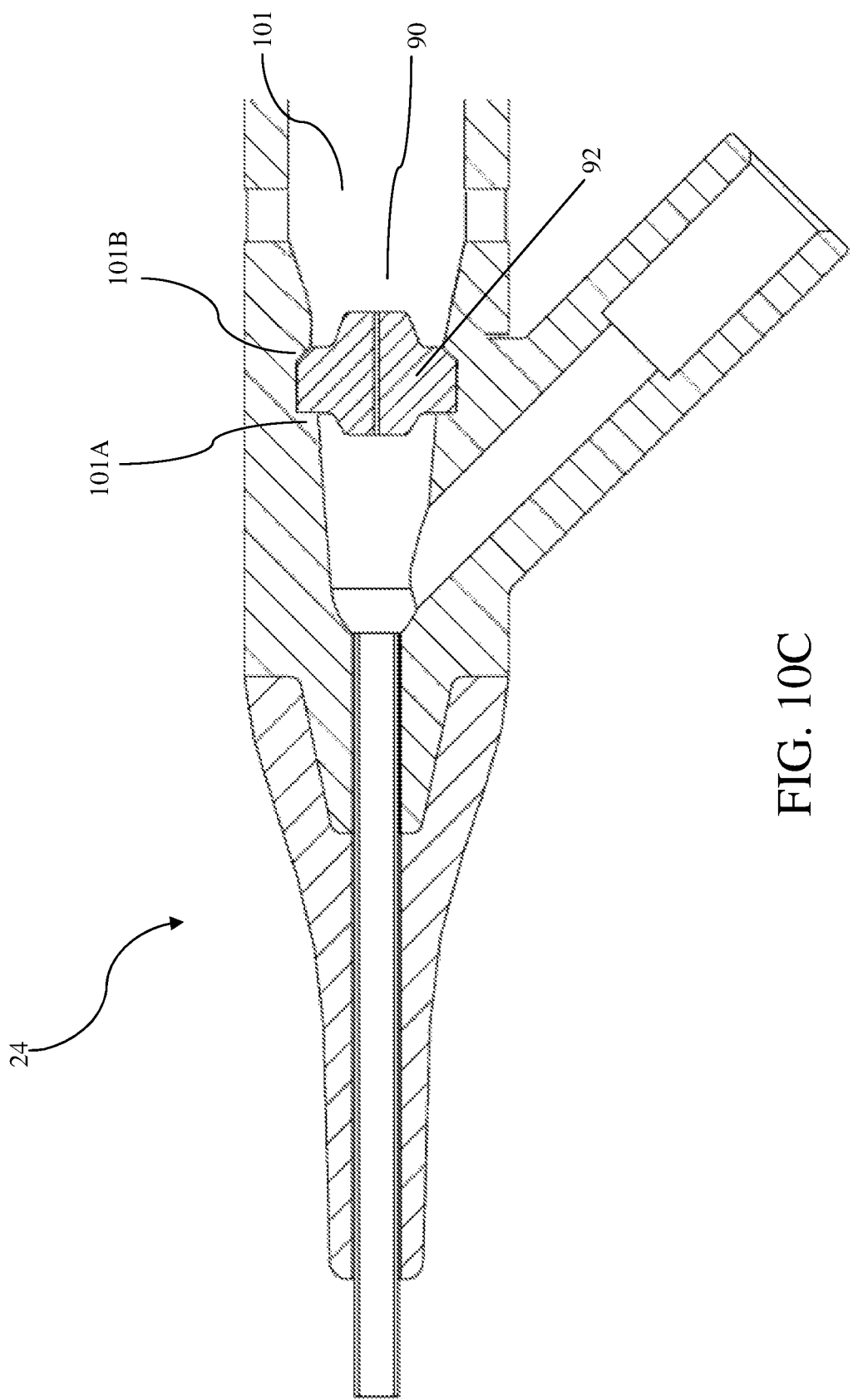
Figure 10D:
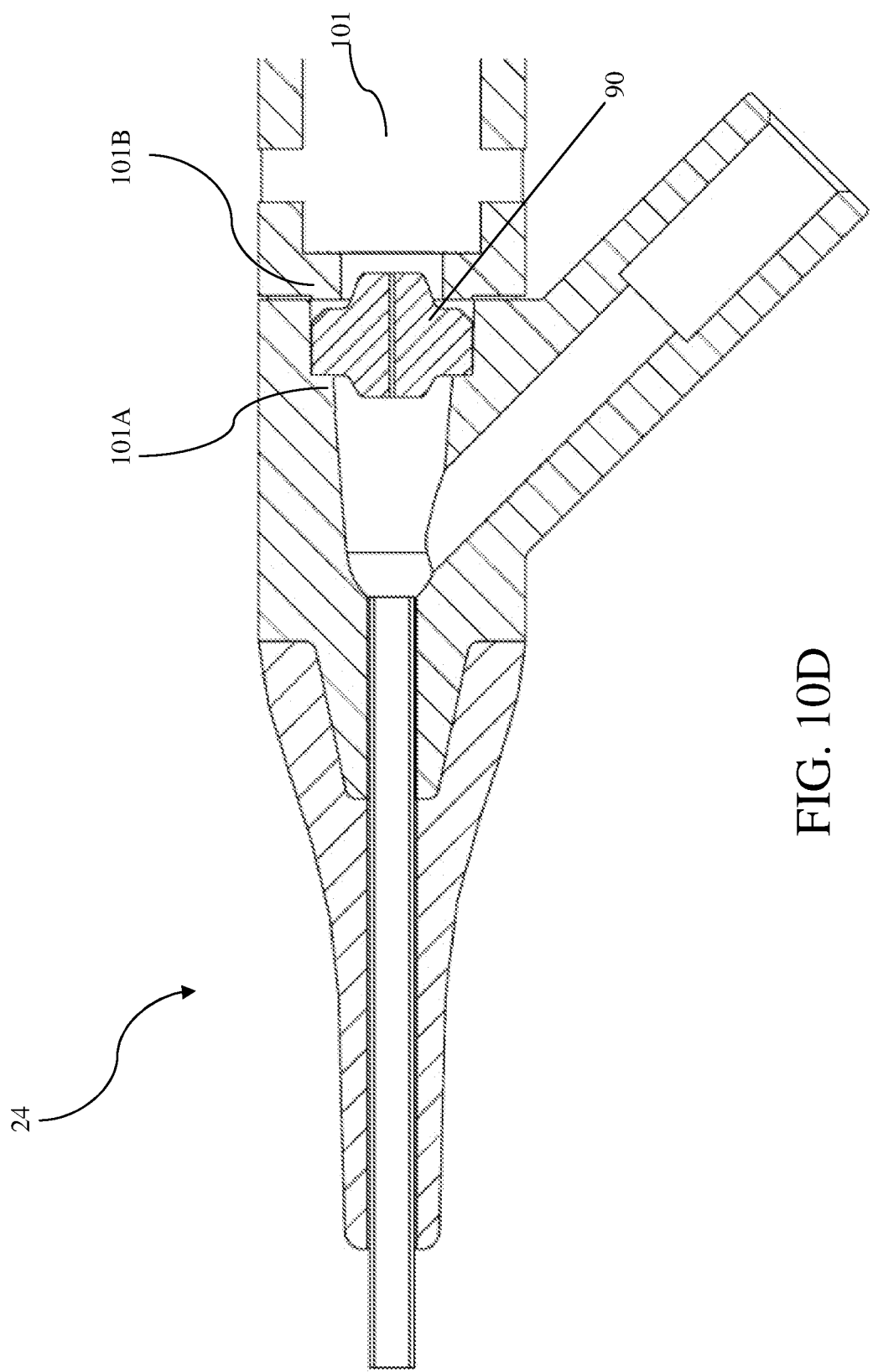

FIGS. 10C and 10D show a septum 90 assembled in the catheter hub 24. In one embodiment, as shown in FIG. 10C the septum 90 is disposed at the distal end of a lumen 101 of the catheter hub 24, which lumen is to accept the safety cap 26. The lumen 101 has a step 101A where the inner diameter of the lumen 101 drops distally. Proximal to the step 101A, the outer diameter of the main body 92 of the septum 90 is big enough to provide a fluid-sealing contact with the inner surface of the lumen 101 of the catheter hub 24. Distal to the step 101A, the first protrusion 94 of the septum 90 extends into the lumen 101 distal to the step 101A. To be understood, the septum can also be disposed in other positions within the lumen 101 of the catheter hub 24. In another embodiment as shown in FIG. 10D, the septum 90 is sandwiched between two steps 101A and 101B formed in the inner surface of the lumen 101 of the catheter hub 24.

In one embodiment, the septum 90 is made of polyisoprene, silicone rubber, polyurethane, butyl rubber or latex.

Figure 11A:
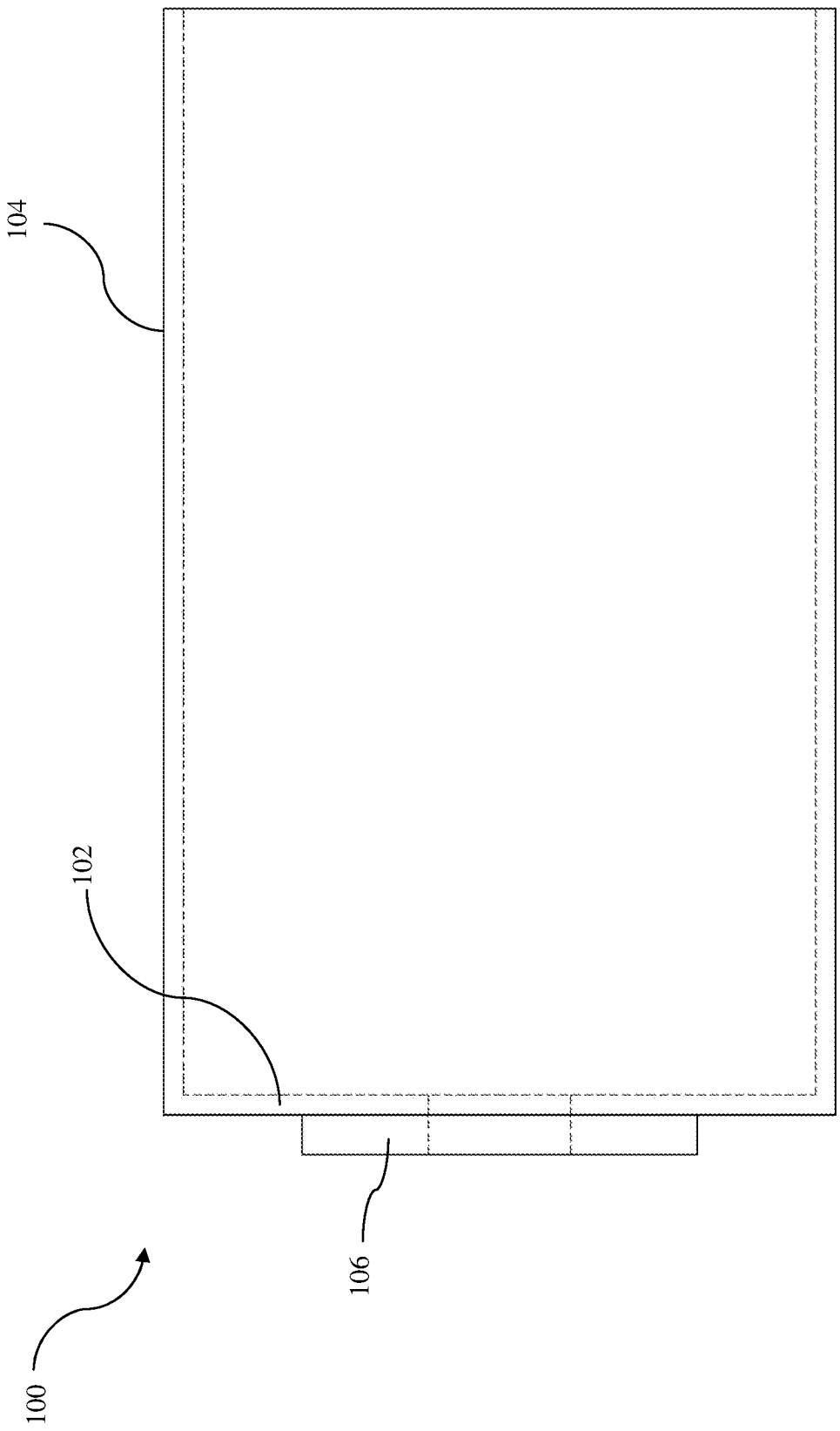
FIGS. 11A and 11B show various views of a septum according to one embodiment of the present invention.
Figure 11B:
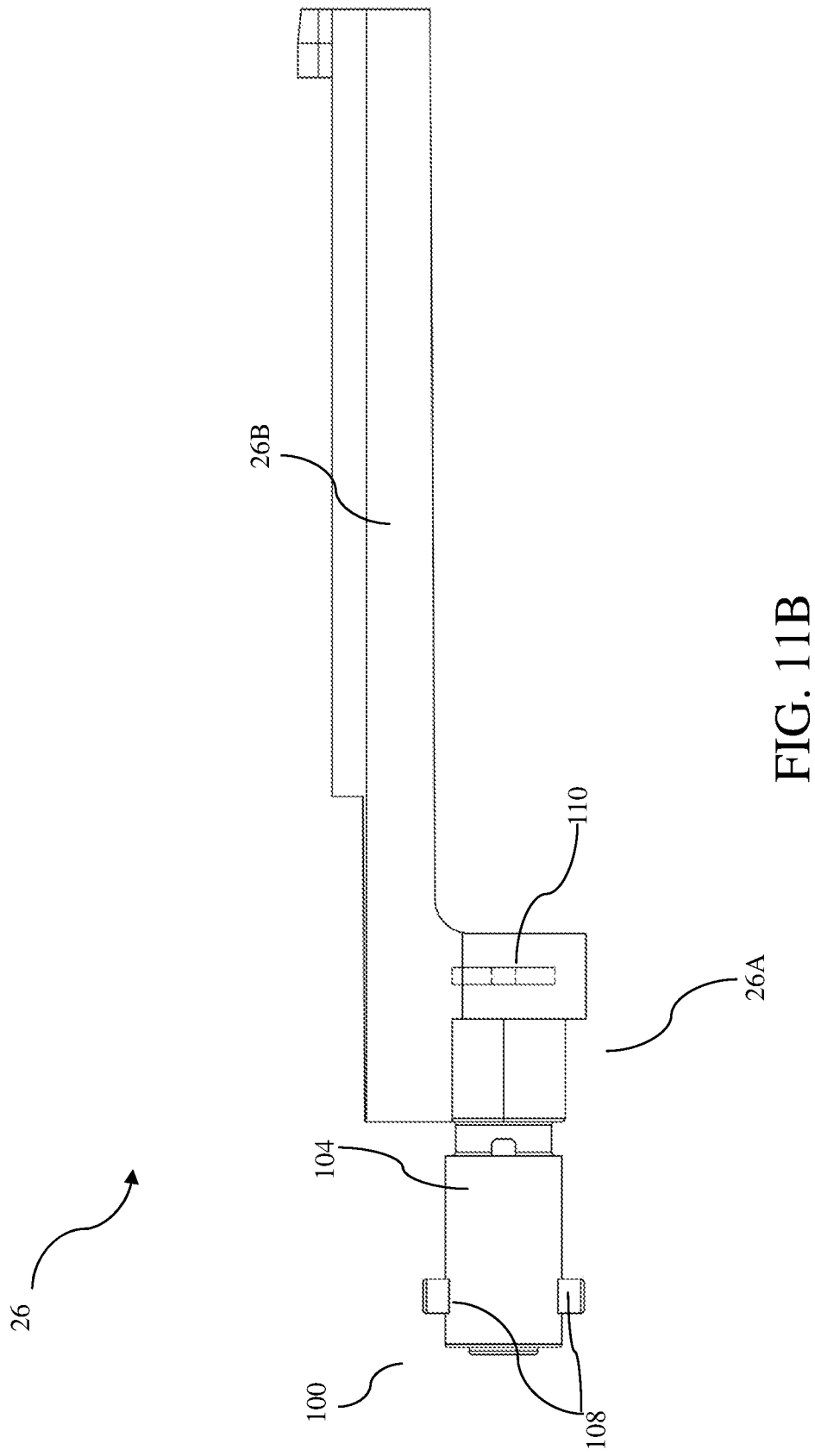

FIGS. 11A and 11B show a septum 100 of one embodiment of the present invention. Referring to FIG. 11A, in one embodiment, the septum 100 comprises a circular end portion 102 and a tubular portion 104 extending from the peripheral of the end portion 102. In one embodiment, the septum 100 is in the shape of a tubular with a close end (circular end portion 102) at the distal end of the septum 100 and an open end at the proximal end of the septum 100. Specifically, in one embodiment, the end portion 102 is a rounded thin film, and the tubular portion 104 extends from the perimeter of the film in a direction perpendicular to the plane of the end portion 102.

In one embodiment, the septum 100 further includes a protrusion 106 extending from a central portion of a surface of the circular end portion 102 opposite to the tubular portion 104. In one embodiment, the protrusion 106 is in the form of a cylinder. In another embodiment, the protrusion 106 is in the form of a circular truncated cone tapering from the bottom surface. The protrusion 106 is coaxial with the circular end portion 102. In one embodiment, the protrusion 106, the circular end portion 102 and the tubular portion 104 form an integral piece.

Similar to the septum 90, the end portion 102 of the septum 100 can be formed with or without a slit.

FIG. 11B shows the septum 100 assembled on the distal portion of the safety cap 26. In one embodiment, the septum 100 is disposed on the fingers of the safety cap 26, wherein the sidewall of the tubular portion 104 includes at least one recess 108 which allows the protrusions disposed on the fingers to extend through the recess 108. In one embodiment, the number and position of the recesses 108 disposed on the tubular portion 104 correspond to the number and position of the protrusion disposed on the fingers of the safety cap 26. As mentioned above, the fingers of the safety cap are separated from each other in the distal portion of the fingers, and are configured to be biased radially when wrapping the needle and to be converged centrally when the needle is pulled out therefrom. The septum 100 is configured to cap/cover the fingers so as to provide a sealing to prevent blood from leaking from the fingers of the safety cap.

Moreover, when the fingers 62 of the safety cap 26 are fully or partially inside the lumen 101 of the catheter hub 24, for example as shown in FIG. 7B, 9 or 10D, the septum 100 disposed on the fingers 62 enhances the sealing between the safety cap 26 and the catheter hub 24. And the septum 100 provides an appropriate friction between the safety cap 26 and the catheter hub 24, and the friction requires the user/clinician to apply a force to separate the catheter hub 24 and the safety cap 26 when the safety cap 26 slides to a locking position that the needle tip is isolated within the safety cap.

In addition, as another embodiment, the septum 100 disposed on the fingers of the safety cap 26 and the septum 90 disposed in the lumen 101 of the catheter hub 24 contacts each other when the safety cap 26 and the catheter hub 24 are connected. Specifically, in one embodiment, the main body 92 or protrusion 94/98 of the septum 90 is in tight contact with the protrusion 106 or end portion 102 of the septum 100 when the finger portion of the safety cap 26 is fully inserted into the lumen 101 of the catheter hub 24. Such a configuration can prevent blood leaking while the needle tip passes through the septa 90 and 100, and accordingly prevent blood exposure when the safety cap 26 and the catheter hub 24 are separated from each other.

In one embodiment, the septum 100 is made of polyisoprene, silicone rubber, polyurethane, butyl rubber or latex.

In one embodiment, as shown in FIG. 11B, the catheter insertion tool 10 further includes a septum 110 disposed in the lumen of the first portion 26A. Specifically, as an embodiment, the septum 110 is in the shape of a cylinder. In one embodiment, the thickness of the septum 110 is configured to be smaller than the distance between the tip and the notch of the needle 18, so as to reduce friction between the septum 110 and the needle 18.

Similar to the septum 90, septum 110 can be formed with or without a slit.

In one embodiment, the outer diameter of the septum 110 is larger than the inner diameter of the lumen of the first portion 26A of the safety cap 26 before the septum 110 is installed in the lumen.

In one embodiment, the septum 110 is disposed in the proximal end of the lumen of the first portion 26A, so as to form a closed cavity together with the septum 100 and the lumen 101. Accordingly, the closed cavity prevents blood from leaking when the needle tip is isolated within the closed cavity of the safety cap 26.

In one embodiment, the septum 110 is made of polyisoprene, silicone rubber, polyurethane, butyl rubber or latex.

Guidewire Advancement Assembly

Referring back to FIG. 2 or FIG. 3A, in one embodiment, the insertion tool 10 comprises a guidewire advancement assembly 30 for distally advancing a guidewire 32 into the vasculature of the patient or proximally withdrawing the guidewire from the vasculature of the patient. In one embodiment, the guidewire advancement assembly 30 further includes a pusher 34 for operating movement of the guidewire 32 in preparation for the advancement of the catheter 22.

Figure 12A:
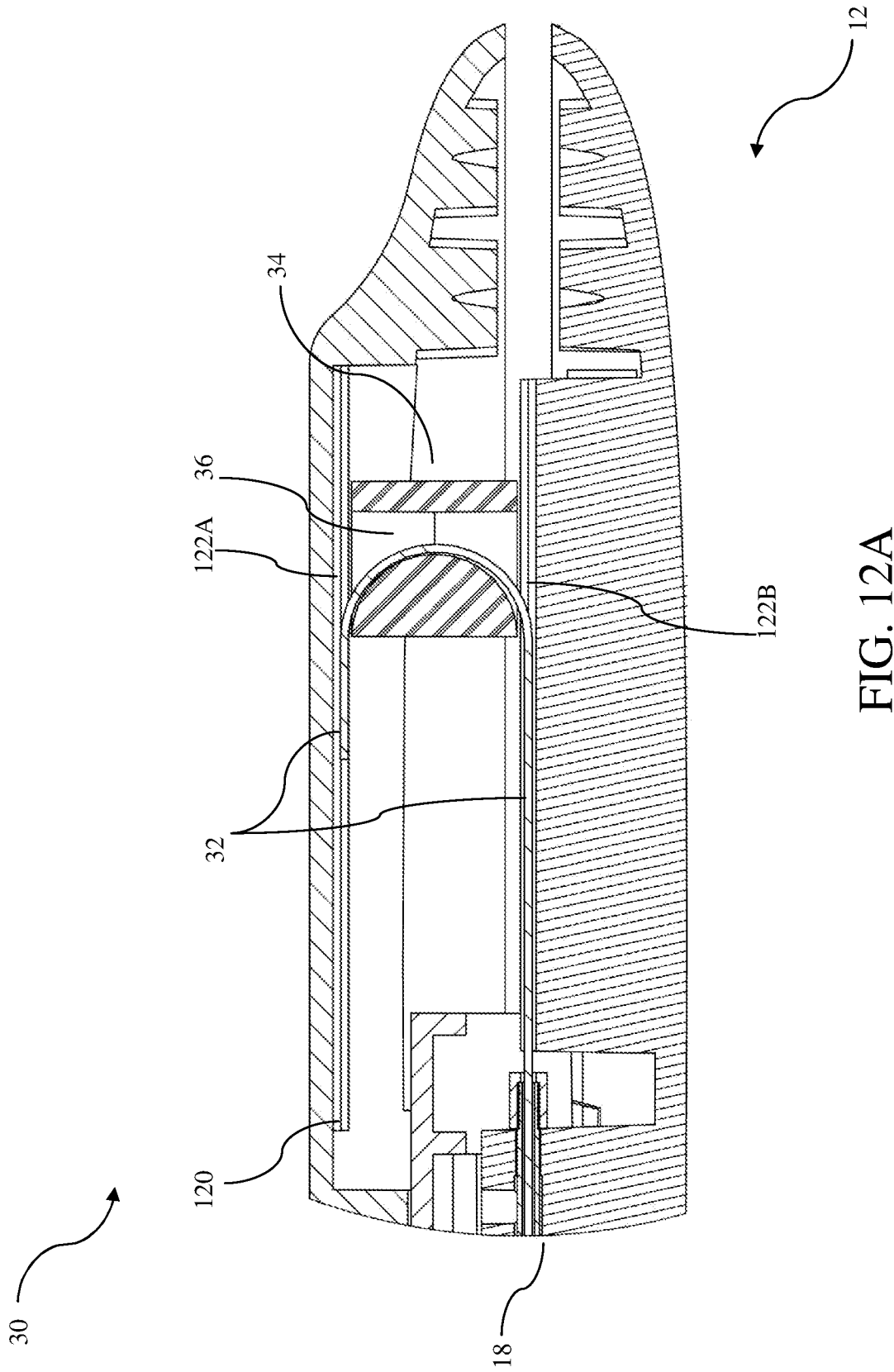
FIGS. 12A and 12B show various views of a guidewire advancement assembly according to one embodiment of the present invention.
Figure 12B:
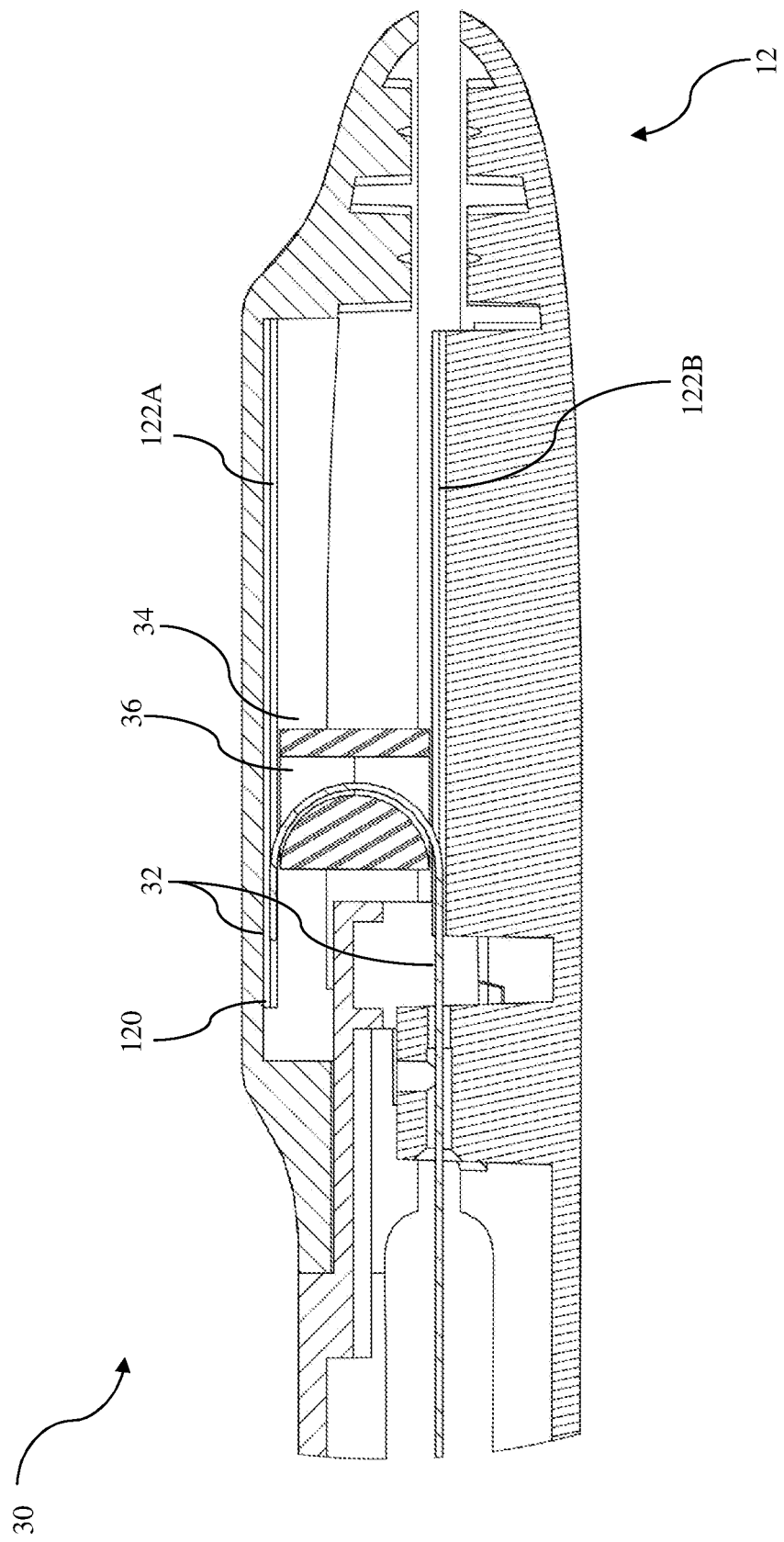

FIGS. 12A and 12B show the sectional view of the guidewire advancement assembly 30 before and after advancing the guidewire 32. In one embodiment, at least a portion of the guidewire 32 is disposed within the lumen of the needle 18. One end of the guidewire 32 is fixated to an anchor point 120 on the housing 12, and the guidewire 32 proximally extends from the anchor point 120, enters a hole 36 of the pusher 34 via a first potion of the rail 122A, extends away from the hole 36, distally extends into a second portion of the rail 122B, and finally extends into the lumen of the needle 18 through the needle base.

In one embodiment, the rail 122A-B includes a groove aligned with the hole 36 in the longitudinal direction of the catheter insertion tool. The groove serves to restrict the guidewire 32 and prevents unwanted waggle or bending of the guidewire 32 during operation. Specifically, as an embodiment, the anchor point 120 and the first portion of the rail 122A is disposed on an inner surface of the first portion 12A of the housing 12. The anchor point 120, the first portion of the rail 122A and the upper opening of the hole 36 of the pusher 34 are arranged in a line, which allows the guidewire 32 to straightly extend from the anchor point 120 to the hole 36. The second portion of the rail 122B is disposed on an inner surface of the second portion 12B of the housing 12. The bottom opening of the hole 36, the second portion of the rail 122B and the proximal end of the needle 18 are arranged in a line, which allows the guidewire 32 to straightly extend from the hole 36 into the lumen of the needle 18. In another embodiment, at least a part of the rail 122A-B is a pipe.

FIG. 12A shows the configuration of the guidewire advancement assembly 30 before operation, where the pusher 34 is positioned close to the proximal end of the housing. When the pusher 34 is distally moved to a position close to the needle base as shown in FIG. 12B, the guidewire 32 is distally advanced over a distance two times the moving distance of the pusher 34.

Figure 13A:
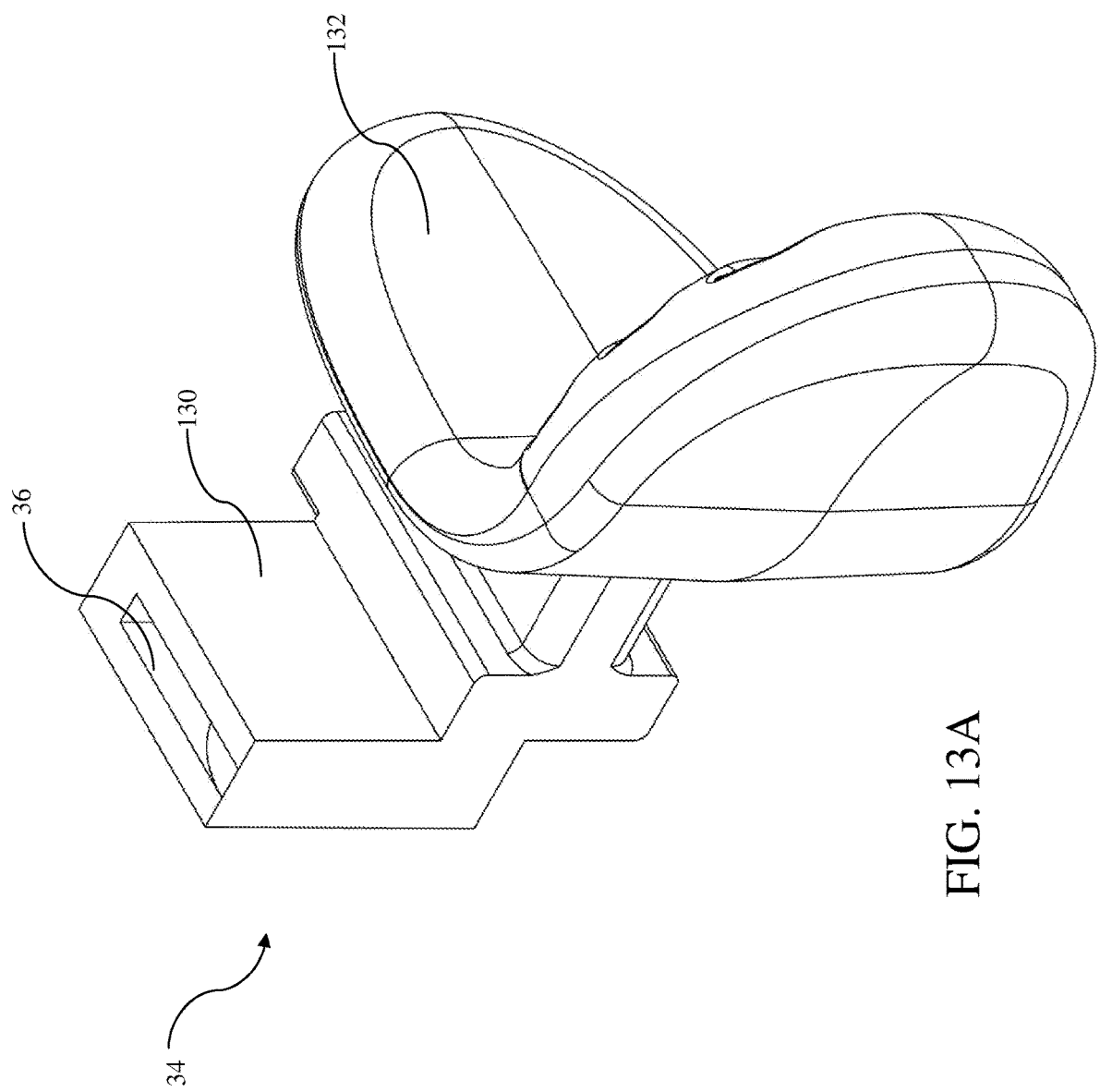
FIGS. 13A-13C show various views of a guidewire pusher according to one embodiment of the present invention.
Figure 13B:
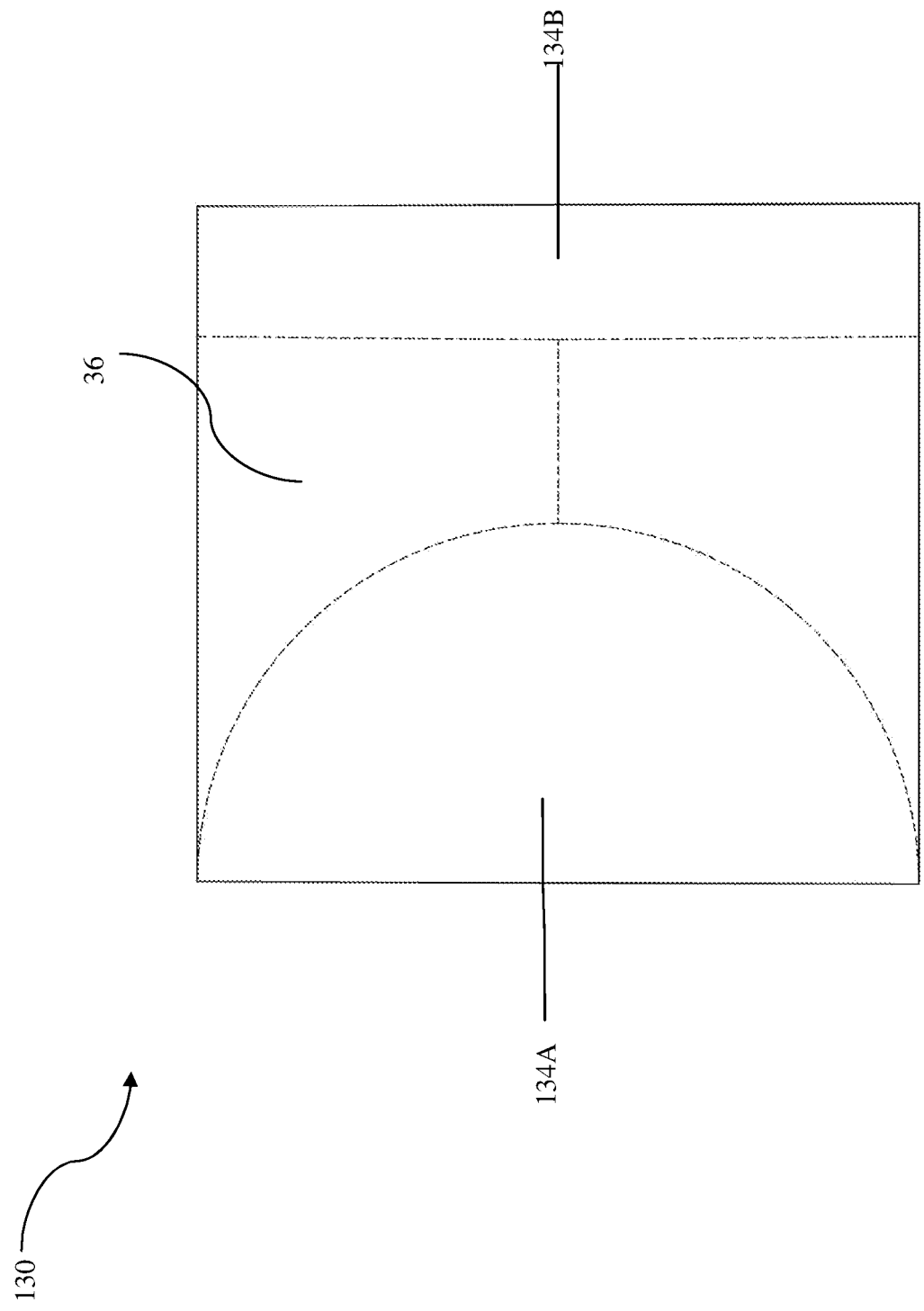
Figure 13C:
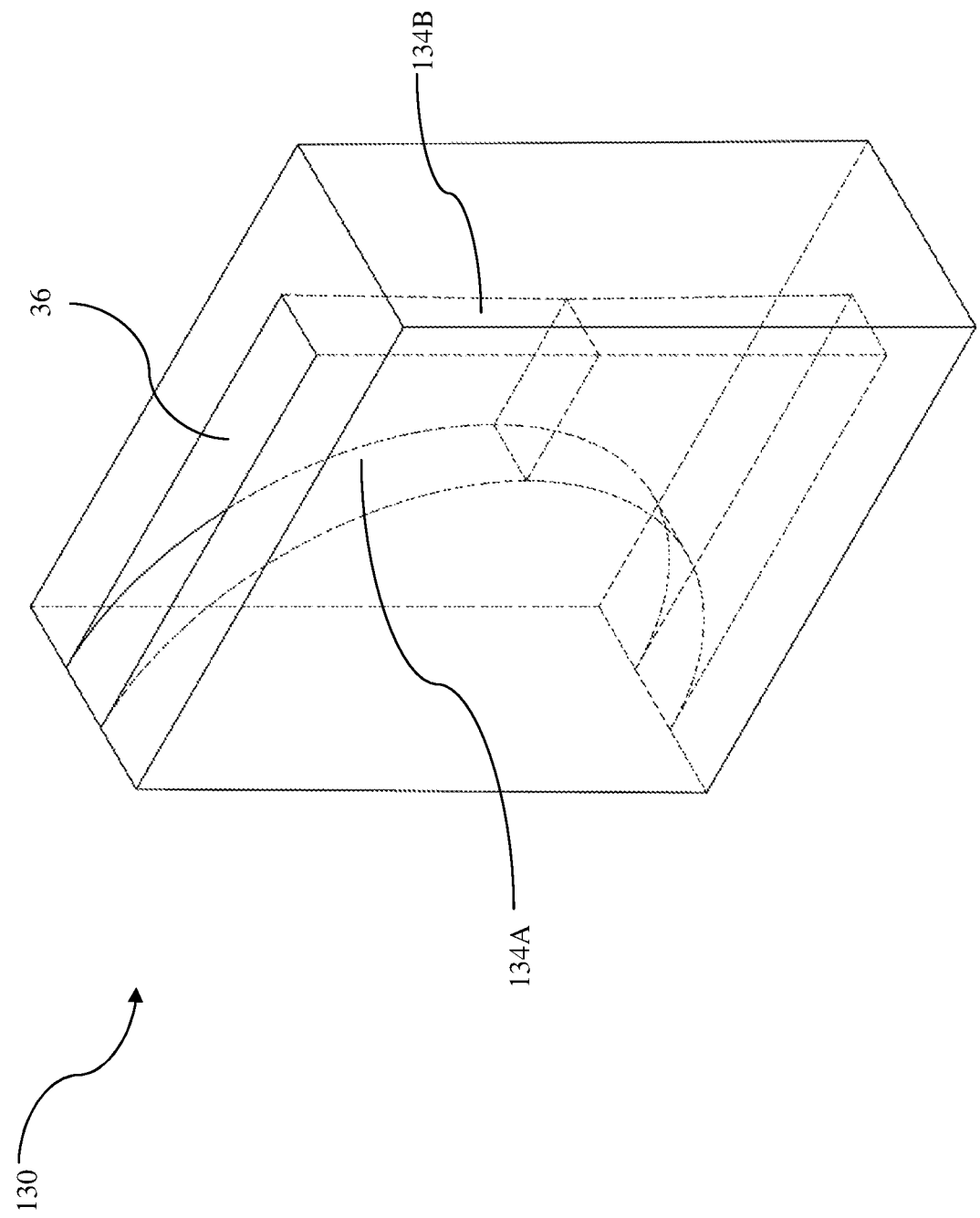

FIGS. 13A-13C shows the structure of pusher 34. FIG. 13A is a perspective view of one embodiment of the pusher 34, where the pusher 34 includes a pushing block 130 and a slider 132. In one embodiment, the pushing block 130 includes a hole 36 extending through the pushing block 130 from a top surface to a bottom surface of the pushing block 130.

FIG. 13B is a sectional view of the pushing block 130, and FIG. 13C is a perspective view of the pushing block 130. As shown in FIGS. 13B and 13C, the pushing block 130 includes four sidewalls defining the hole 36. In one embodiment, the four sidewalls of the hole 36 includes a first sidewall 134A in the form of a planar curve, and a straight second sidewall 134B opposite to the first sidewall. The minimum distance between the first and second sidewalls 134A and 134B is wide enough to allow free longitudinal movement of a guidewire 32 and is narrow enough to restrict sway of the guidewire 32. In another embodiment, the second sidewall 134B is also in the form of a planar curve, wherein the planar surface of the second sidewall 134B is in parallel to the planar surface of the first sidewall 134A. In one embodiment, the other two sidewalls are straight.

Referring back to FIG. 2 and FIG. 13A, in one embodiment, the slider 132 is connected to the pushing block 130, the pushing block 130 is disposed inside the housing 12 and the slider 132 is partially disposed outside the housing 12. In one embodiment, a slit is formed between the second portion 13B of the housing and the proximal portion of the first portion 13A of the housing, which clamps the connection part between the pushing block 130 and the slider 132, and allows the pusher 34 slide with respect to the housing 12.

Figure 14A:
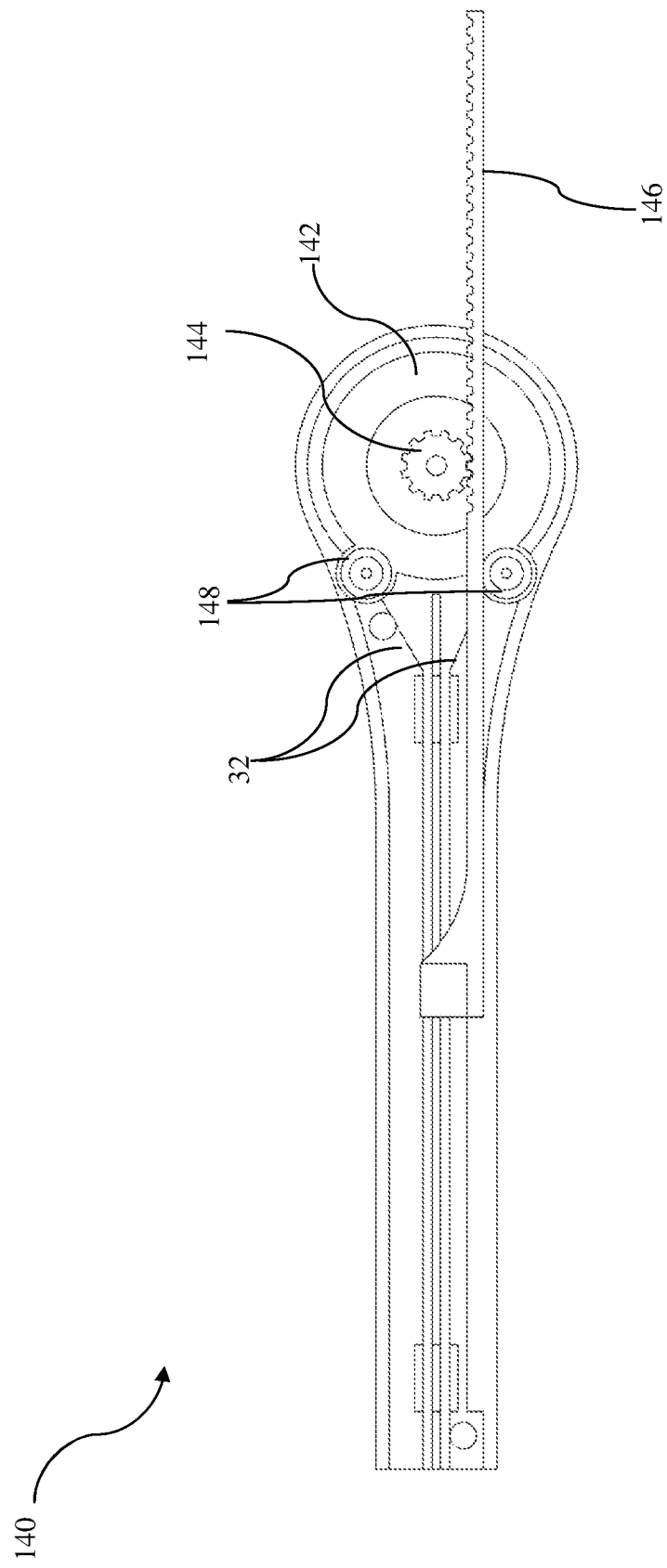
FIGS. 14A and 14B show various views of a guidewire advancement assembly according to one embodiment of the present invention.
Figure 14B:
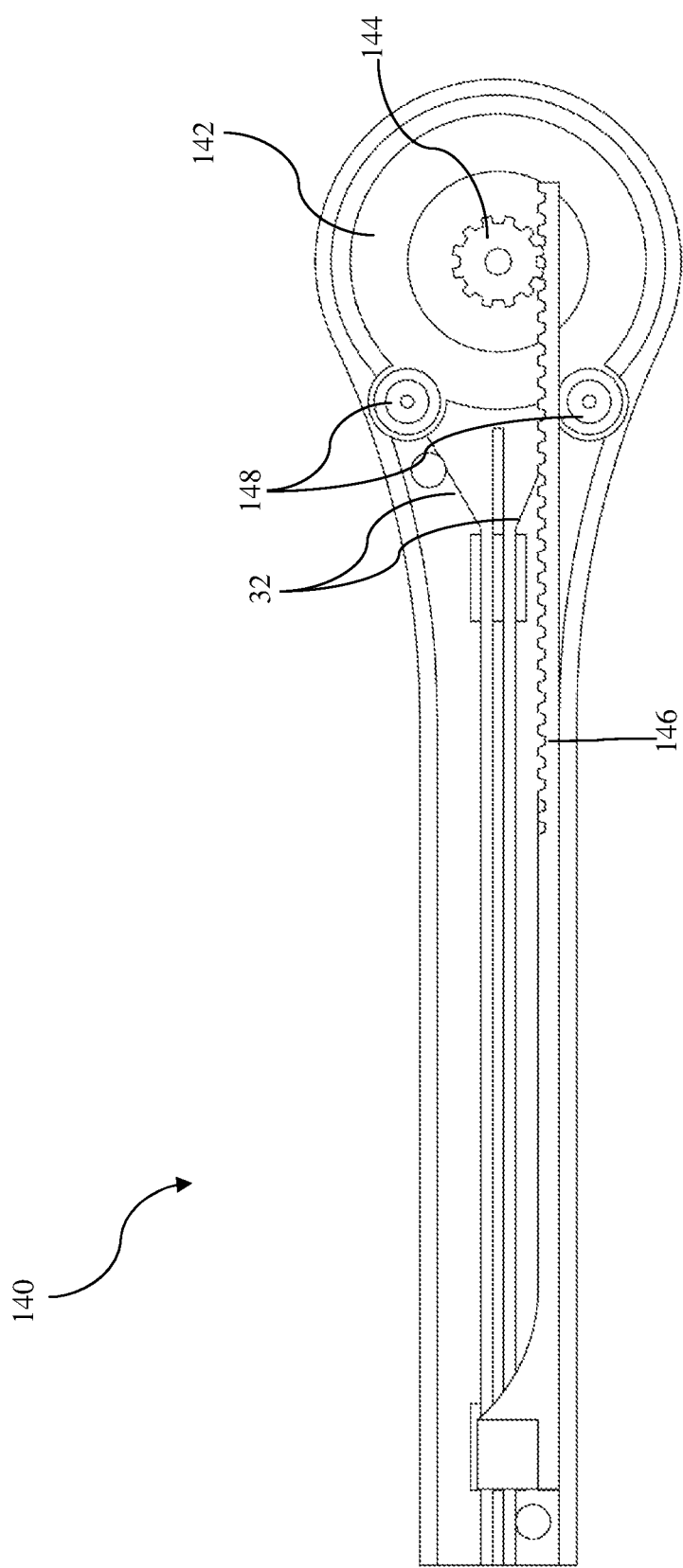

FIGS. 14A and 14B show another embodiment of the guidewire advancement assembly 140 of the present invention. In one embodiment, the guidewire advancement assembly 140 includes a wheel 142 and a gear 144, wherein the gear 144 is fixated to the wheel 142 coaxially. The rotation of the gear 144 synchronously drives the rotation of the wheel 142. In one embodiment, a guidewire 32 is partially rolled around the outer diameter of the wheel 142.

In one embodiment, the guidewire advancement assembly 140 further includes a rack 146, which engage with the gear 144 through the engagement between the teeth of the rack 146 and the teeth of the gear 144. In one embodiment, a distal end of the rack 146 is slidably attached to a rail disposed on the housing. The sliding movement of the rack 146 along the rail drives the rotation of the gear 144 and the rotation of the wheel 142, and the guidewire 32 is accordingly driven around the wheel 142.

In one embodiment, the guidewire advancement assembly 140 further includes at least one idler 148 for restricting the guidewire 32 against the peripheral surface of the wheel 142. In one embodiment, at least the peripheral surface of the wheel 142 is configured to provide sufficient friction for preventing skid between the wheel 142 and the guidewire 32. This can be done by way of special treatment of the peripheral surface or by selecting a proper material to form the surface.

In one embodiment, the guidewire advancement assembly 140 further includes a pipe rail for guiding the movement of the guidewire 32.

The advancement efficiency of the guidewire advancement assembly 140 depends on the ratio between the diameter of the gear 144 and the wheel 142. For example, if the ratio between the diameter of the gear 144 and the wheel 142 is 1:3, the ratio between the sliding distance of the rack 146 and the moving distance of the guidewire is also 1:3.

Operation Procedures

FIGS. 4A-5C depict various stage of the operation of the insertion tool 10 to place the catheter 22 into the vasculature of a patient. For clarity, the various stages are depicted without actual insertion into a patient being shown. With the insertion tool 10 in the configuration shown on FIG. 2, a user grasping the insertion tool 10 first guides the distal portion needle 18 through the patient's skin at a suitable insertion site and accesses a subcutaneous vessel. Confirmation of proper vessel access having been achieved is evident via blood flash, i.e., the presence of blood between the outer diameter of the needle 18 and the inner diameter of the catheter 22 due to blood passing out of the notch from the hollow interior of the needle. Note that in one embodiment, the presence of blood in the safety cap 26 serves as a secondary blood flash indicator due to blood entering the housing from the needle 18 when the vessel is accessed.

After needle access to the vessel is confirmed, the user operates the guidewire advancement assembly 30 or 140. In one embodiment, as to the guidewire advancement assembly 30 shown in FIGS. 12A-13C, the pusher 34 is distally slid by the finger of the user to distally advance the guidewire 32, which is initially disposed within the hollow needle 18. In another embodiment, as to the guidewire advancement assembly 140 shown in FIGS. 14A-14B, the rack 146 is distally slid by the finger of the user to distally advance the guidewire 32. The distal advancement of the guidewire continues until the pusher 34 has been distally slid its full travel length, resulting in a predetermined length of the guidewire 32 extending past the distal end of the needle 18.

In one embodiment, further distal advancement of the pusher 34 is prevented when the pushing block 130 contacts the needle base.

Once the guidewire 32 has been fully extended within the vessel of the patient, the user operates the catheter advancement assembly 20, wherein the catheter hub 24 is distally advanced by the user to cause the catheter 22 to slide distally over the needle 18 and the guidewire 32 and into the patient's vasculature via the insertion site. At this stage, further distal movement of the catheter hub and the catheter is prevented by the distal portion of the housing. The user then may slide the distal part of the first portion of the housing with respect to the second portion of the housing to release the engagement between the two housing portions. After the release, further distal movement of the catheter hub and the catheter is allowed. To be noted, during the distal sliding of the catheter hub 24, since the safety cap 26 is initially engaged with the catheter hub 24, the safety cap 26 also slides with the catheter hub 24.

After the catheter 22, catheter hub 24 and safety cap 26 are released from the housing, the user may further advance the catheter hub 24 distally and withdraw the needle 18 from the body of the patient. These two movements can be operated simultaneously or successively. Distal movement of the catheter hub and the safety cap relative to the needle or the housing is stopped when the safety cap is locked to the locking point and the needle tip is isolated within the safety cap.

With the needle tip withdrawn from the fingers of the safety cap and stopped inside the lumen of the first portion of the safety cap, the catheter hub 24 is free to be separated from the safety cap by the user. As mentioned, the septa in the catheter cap and the safety cap prevents exposure of blood of the patient. Then the catheter 22 remain in the body of the patient, the catheter hub 24 remains close to the insertion site, and the housing 12, needle 18, safety cap 26 and guidewire advancement assembly can be removed.

In one embodiment the insertion tool 10 of the present invention can include a cap or other protective device that is removably attached to the insertion tool before use so as to protect the needle and catheter.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

The invention claimed is:

1. A catheter insertion tool, comprising:
a housing including a rail fixed to the housing;
a needle distally extending from the housing; and
a safety cap slidable along the needle, wherein the safety cap is configured to be locked to the housing when distally sliding to a position of isolating a tip of the needle within the safety cap, the safety cap comprising:
a first portion wrapping the needle; and
a second portion comprising a lever slidably attached to a-the rail, the lever including two vertical walls respectively extending from two sides of a surface of the lever facing the rail, each of the two vertical walls including an inward facing protrusion, the inward facing protrusion configured to be locked within a notch formed on the rail to lock the safety cap to the housing when the safety cap distally slides to the position of isolating the tip of the needle within the safety cap.

2. The catheter insertion tool according to claim 1, wherein the safety cap is locked to the housing when distally sliding to the position of isolating the tip of the needle within the safety cap by means of being locked to the rail.

3. The catheter insertion tool according to claim 2, further comprising a catheter hub, which is connected to the safety cap until the safety cap is locked to the housing when distally sliding to the position of isolating the tip of the needle.

4. The catheter insertion tool according to claim 3, wherein the first portion of the safety cap comprises at least two fingers which are configured to be biased radially toward an inner surface of the catheter hub when a stem of the needle extends through the first portion of the safety cap and to be released from a biased position when the safety cap distally slides to the position of isolating the tip of the needle.

5. The catheter insertion tool according to claim 4, wherein each of the at least two fingers includes a protrusion, which is inserted into a groove disposed on the inner surface of the catheter hub when the at least two fingers are biased radially toward the inner surface of the catheter hub when the stem of the needle extends through the first portion of the safety cap.

6. The catheter insertion tool according to claim 3, wherein the first portion of the safety cap comprises at least two fingers, which remain in a same position when the stem of the needle extends through the first portion of the safety cap and when the safety cap distally slides to the position of isolating the tip of the needle.

7. The catheter insertion tool according to claim 6, wherein each of the at least two fingers includes a protrusion, which is inserted into a recess disposed on an inner surface of the catheter hub.

8. The catheter insertion tool according to claim 7, wherein a proximal side of each protrusion forms an obtuse angle relative to a surface of a respective finger of the at least two fingers where the proximal side extends from the respective finger.

9. The catheter insertion tool according to claim 1, wherein the safety cap is locked to the housing at a first location of the safety cap and the tip of the needle is isolated within a second location of the safety cap when the safety cap slides to the position of isolating the tip of the needle within the safety cap, the first position being distally spaced from the second position.

10. The catheter insertion tool according to claim 1, wherein a tactile sensation for a clinician is produced when the safety cap is locked to the housing.

11. The catheter insertion tool according to claim 1, wherein the notch is formed between two prominent bumps disposed on the rail.

12. The catheter insertion tool according to claim 11, wherein a proximal one of the two prominent bumps has an inclined slope at a proximal side and is substantially vertical to a surface of the rail at a distal side.

13. The catheter insertion tool according to claim 11, wherein a distal one of the two prominent bumps is raised higher from a surface of the rail than a proximal one of the two prominent bumps.

14. The catheter insertion tool according to claim 1, wherein the two vertical walls extends throughout a full length of the lever.

* * * * *